US008444660B2

(12) United States Patent
Adams et al.

(10) Patent No.: US 8,444,660 B2
(45) Date of Patent: May 21, 2013

(54) DEVICE AND METHOD FOR THROUGH THE SCOPE ENDOSCOPIC HEMOSTATIC CLIPPING

(75) Inventors: Mark L. Adams, Stoughton, MA (US); Russell F. Durgin, Attleboro, MA (US); Vincent Turturro, Marlboro, MA (US); Justin Grant, Hopkinton, MA (US); Norman May, Franklin, MA (US); Roy H. Sullivan, III, Millville, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 291 days.

(21) Appl. No.: 13/009,094

(22) Filed: Jan. 19, 2011

(65) Prior Publication Data

US 2011/0112551 A1    May 12, 2011

Related U.S. Application Data

(60) Continuation of application No. 11/036,421, filed on Jan. 14, 2005, now Pat. No. 7,879,052, which is a division of application No. 09/971,488, filed on Oct. 5, 2001, now Pat. No. 7,094,245.

(51) Int. Cl.
*A61B 17/122* (2006.01)
(52) U.S. Cl.
USPC ............................................. 606/157

(58) Field of Classification Search
USPC ................ 606/120, 139, 142, 143, 157, 158, 606/213, 215; 24/115 F, 456, 537, 602
See application file for complete search history.

(56) References Cited

U.S. PATENT DOCUMENTS

| | | | | |
|---|---|---|---|---|
| 3,958,576 | A | * | 5/1976 | Komiya ...................... 606/142 |
| 4,367,746 | A | * | 1/1983 | Derechinsky ................. 606/142 |
| 4,383,350 | A | * | 5/1983 | Coty ............................. 24/669 |
| 4,681,107 | A | * | 7/1987 | Kees, Jr. ....................... 606/142 |
| 5,015,249 | A | * | 5/1991 | Nakao et al. .................. 606/142 |
| 5,242,456 | A | * | 9/1993 | Nash et al. .................... 606/142 |
| 5,618,307 | A | * | 4/1997 | Donlon et al. ................ 606/205 |
| 5,634,932 | A | * | 6/1997 | Schmidt ........................ 606/157 |
| 5,766,189 | A | * | 6/1998 | Matsuno ....................... 606/158 |
| 5,792,149 | A | * | 8/1998 | Sherts et al. .................. 606/142 |
| 5,867,877 | A | * | 2/1999 | Patterson et al. ............ 24/598.5 |
| 5,897,565 | A | * | 4/1999 | Foster ........................... 606/158 |
| 6,386,496 | B1 | * | 5/2002 | Lai et al. ..................... 248/309.1 |
| 6,814,742 | B2 | * | 11/2004 | Kimura et al. ................ 606/151 |
| 6,991,634 | B2 | * | 1/2006 | Sugiyama et al. ............ 606/142 |
| 2002/0151916 | A1 | * | 10/2002 | Muramatsu et al. .......... 606/158 |

* cited by examiner

*Primary Examiner* — Ryan Severson
(74) *Attorney, Agent, or Firm* — Fay Kaplun & Marcin, LLP

(57) ABSTRACT

Medical device used to cause hemostasis of blood vessels using a clip arrangement delivered to a target region through an endoscope. Method for using the device to cause hemostasis of a blood vessel through an endoscope. Medical device including a reversibly closeable clip, a locking arrangement, a control wire, a sheath, and a handle with an actuating trigger. Through the endoscope, hemostatic clipping device that is fully reversible and lockable. Hemostatic clip that reversibly targets and clips bleeding ulcers.

18 Claims, 27 Drawing Sheets

Overlapped
Perpendicular
Tongue & Groove
Parallel-Horizontal
Parallel-Vertical
Parallel-Positive Angle
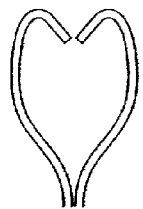
Parallel-Negative Angle
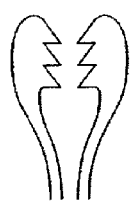
Saw Toothed
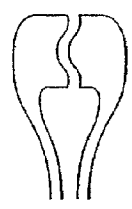
Matching Wave
Multi-Length Horizontal
FIG. 8F

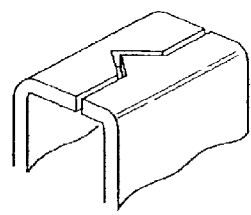
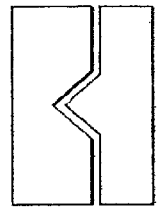
Single-Tooth Pointed
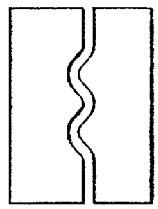
Multi-Toothed Waved
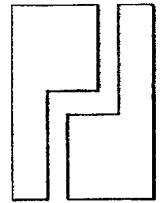
Offset-L Tooth
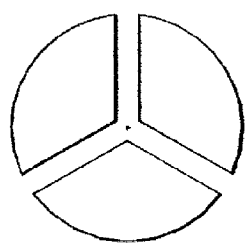
Multi-Jaw Pointed
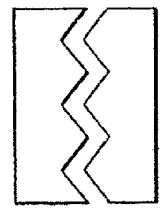
Multi-Tooth Pointed
FIG. 8G

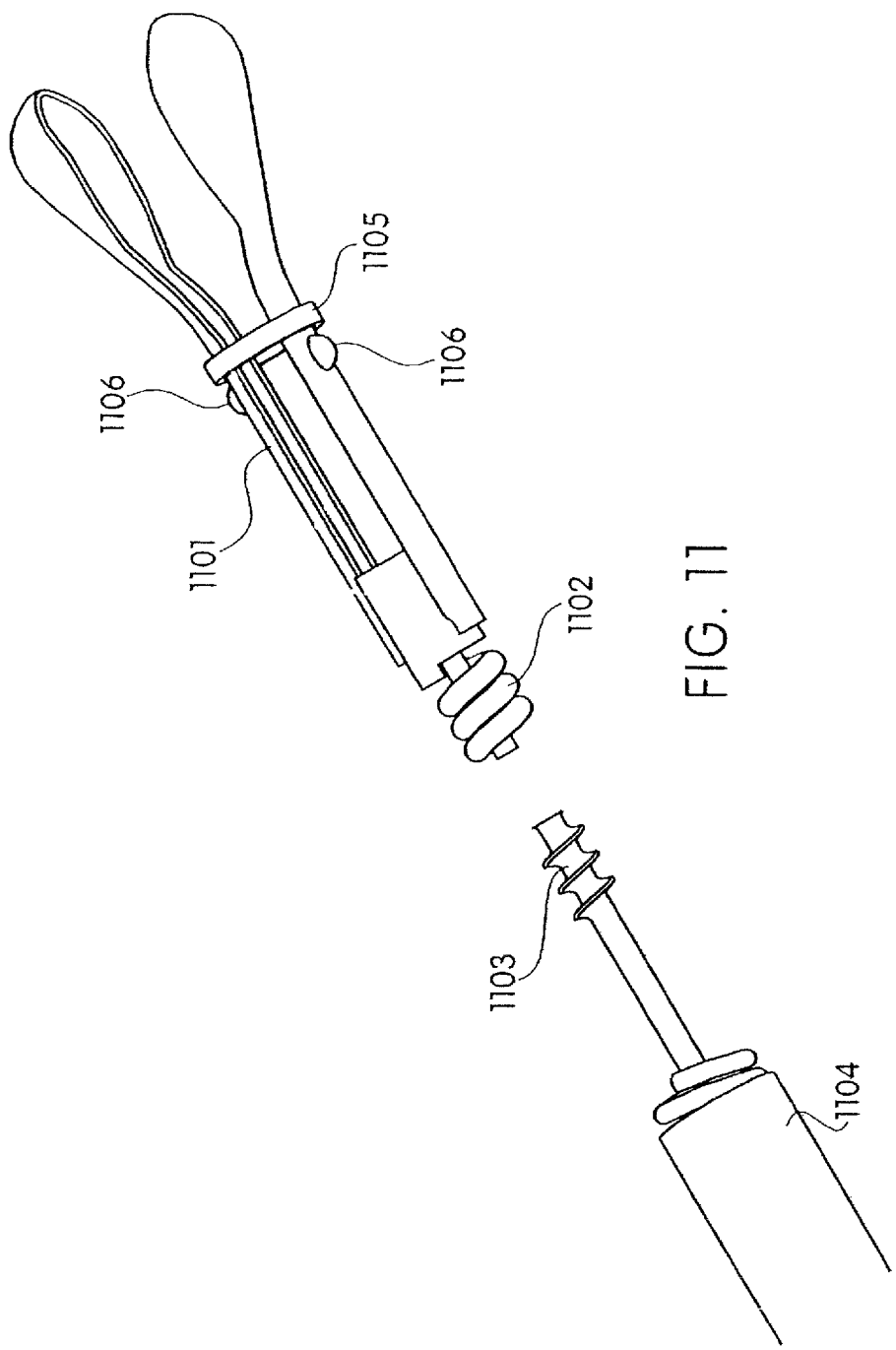

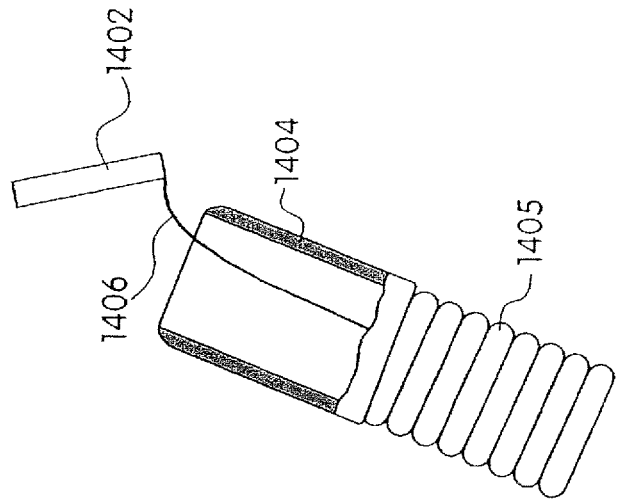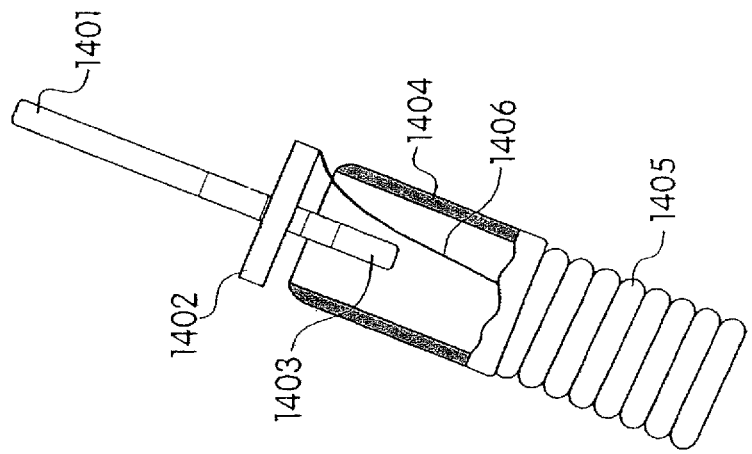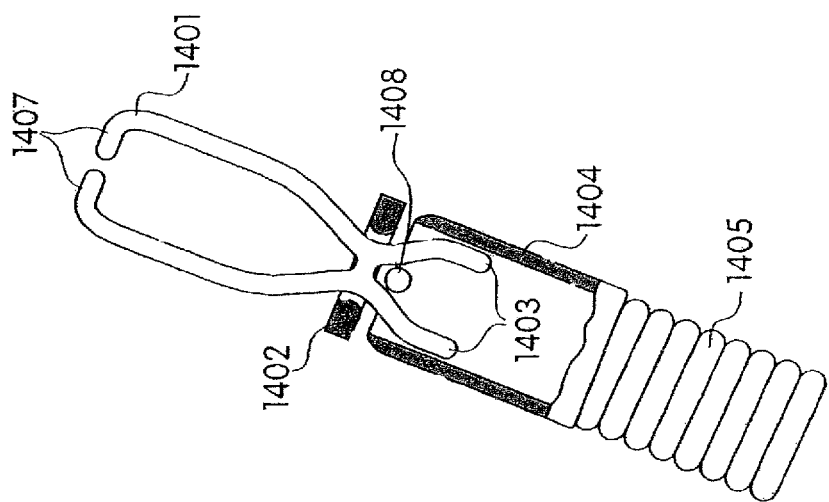

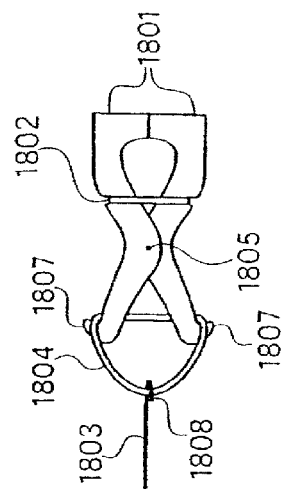
FIG. 18C
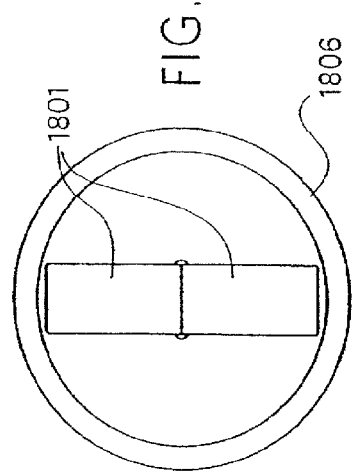
FIG. 18E
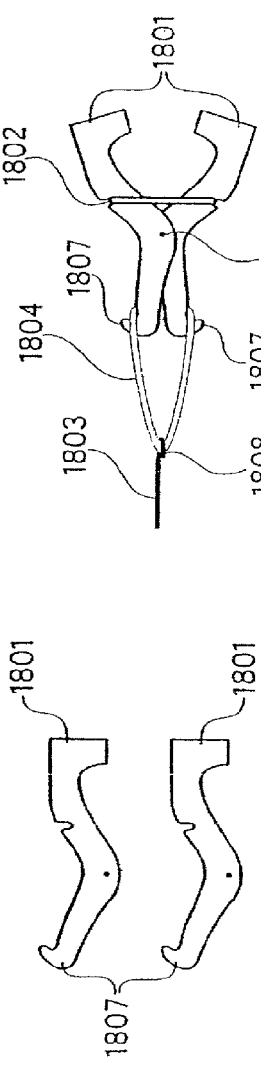
FIG. 18B
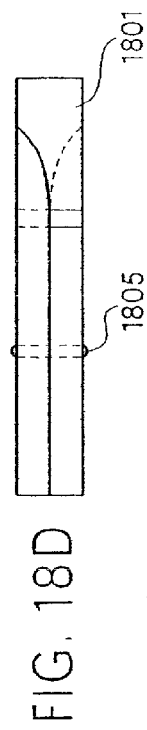
FIG. 18D
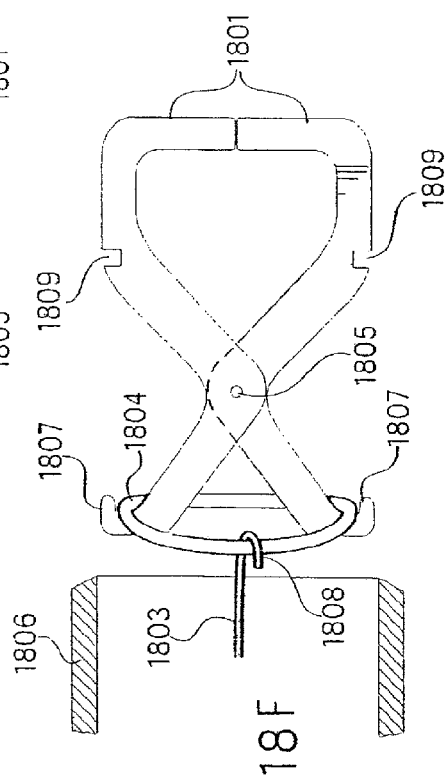
FIG. 18A
FIG. 18F

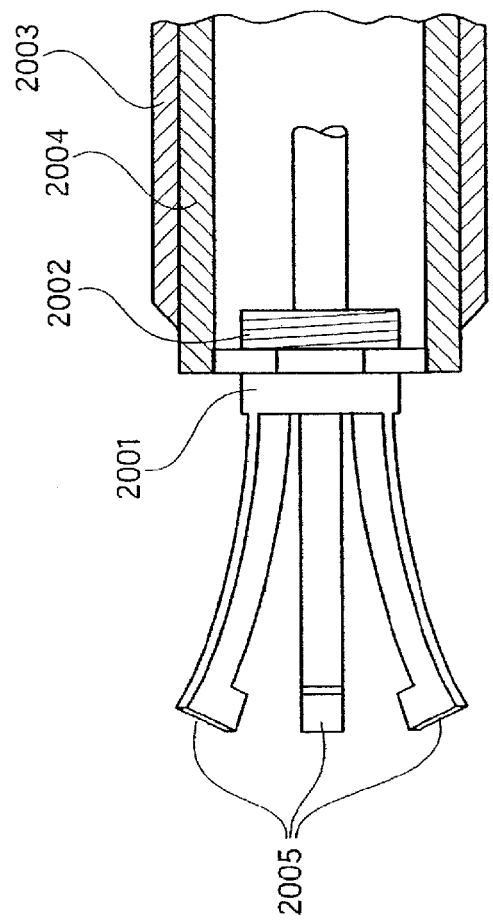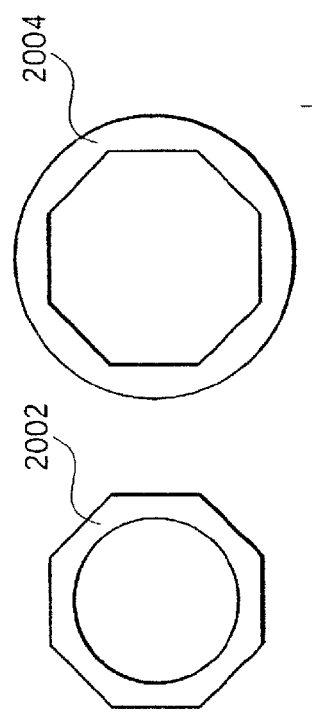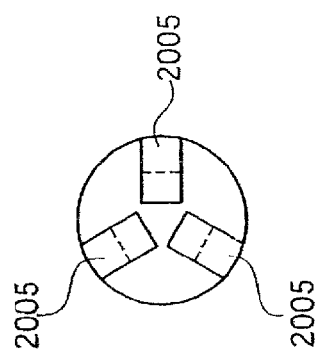
FIG. 20B
FIG. 20C
FIG. 20A

… DEVICE AND METHOD FOR THROUGH THE SCOPE ENDOSCOPIC HEMOSTATIC CLIPPING

PRIORITY CLAIM

The present application is a Continuation of U.S. patent application Ser. No. 11/036,421 filed on Jan. 14, 2005; which is a Divisional of U.S. patent application Ser. No. 09/971,488 filed on Oct. 5, 2001 now U.S. Pat. No. 7,094,245, the entire disclosure of these applications are expressly incorporated herein by reference.

FIELD OF THE INVENTION

The present invention relates to compression clips, and more specifically, to compression clips used to cause hemostasis of blood vessels located along the gastrointestinal tract delivered to a target site through an endoscope.

BACKGROUND

Gastrointestinal ("GI") bleeding is often associated with peptic ulcer disease (PUD) and can be fatal if not treated immediately. Hemorrhaging is the most dangerous procedure with which a Gastro-Intestinal Endoscopist has to deal. It is his/her only unplanned, emergency procedure where time is critical in determining the outcome. It is also the one problem the Endoscopist faces that is generally not an outpatient procedure. A bleeding PUD can be a critical clinical event as there is internal hemorrhaging. Ulcers are classified from clean to active spurting bleeding. The most worrisome are active bleeders and visible vessels. Untreated visible vessels are likely to bleed.

Suspected bleeding PUD patients can be diagnosed and treated endoscopically in an emergency room, an ICU or the GI suite. Surgery generally results in higher cost, morbidity and mortality than endoscopy. Therefore, laparoscopy or open surgery is not preferred unless there is no endoscopic alternative or endoscopy has failed. If the diseased tissue is beyond repair, a surgical gastric resection may be performed.

Currently, the endoscopist has two commonly used treatments and some lesser used therapies to achieve hemostasis of the ulcer. The most widely used treatments are thermal therapy and injection therapy. Some of the less common options are Olympus Endoclips, lasers and argon plasma cautery.

With thermal therapy, a catheter with a rigid heating element tip is passed through the working channel of an endoscope after the bleed is visualized and diagnosed. After the rigid catheter tip has exited the scope, the scope is manipulated to press the tip against the bleed site. Thermal power is applied, either through a resistive element in the tip or by applying RF energy through the tissue, thus desiccating and cauterizing the tissue. The combination of the tip compressing the tissue/vessel and the application of heat theoretically welds the vessel closed.

Although thermal treatment is fairly successful in achieving hemostasis, it often takes more than one attempt (irrigation is applied after the initial treatment to see if hemostasis has occurred) and there is frequent re-bleeding. Generally several pulses of energy are applied during each attempt. If early re-treatment is needed, there is a risk of perforation with the heat probe. Another disadvantage is that both types of thermal therapy require a specialized power generator and the equipment can be expensive.

With injection therapy, a catheter with a distally extendable hypo needle is passed through the working channel of the endoscope after the bleeding has been visualized and diagnosed. Once the catheter tip has exited the scope, the scope is manipulated to the bleed site, the needle is extended remotely and inserted into the bleed site. A vasoconstricting (narrowing of blood vessels) or sclerosing (causing a hardening of tissue) drug is then injected through the needle. Multiple injections in and around the bleeding site are often needed, until hemostasis has been achieved. As with thermal therapy, re-bleeding is also a problem.

The treatment used in any specific instance is highly dependent on geographic region. In some regions, especially in the United States, injection therapy is often combined with thermal treatment since neither therapy is completely effective alone.

The primary success rate of endoscopic treatment is about 90%. The other cases are usually referred to surgery. All identified ulcers may re-bleed at a later time, but the re-bleed rate for endoscopically treated active bleeds and a visible vessel is 10-30%. Even with the introduction of new treatments and devices, these rates have not improved significantly in decades. Surgery's short and long-term success for permanent hemostasis is virtually 100%.

Surgery has a higher success rate because the bleeding site is compressed mechanically, causing better hemostasis. Using devices such as clamps, clips, staples, sutures (i.e. devices able to apply sufficient constrictive forces to blood vessels so as to limit or interrupt blood flow), the bleeding vessel is ligated or the tissue around the bleed site is compressed, ligating all of the surrounding vessels.

An existing device that incorporates the advantages of surgery into a less-invasive endoscopic procedure is the Olympus EndoClip. The goal of the device is to pinch the bleeding vessel to create hemostasis. The problem with this device is that once jaw closure begins, it is not possible to reopen them, and the endoscopist is committed to firing the clip. In other words, jaw closure is not reversible. Because the vessel is frequently difficult to see, often several clips must be deployed in order to successfully pinch the vessel and achieve hemostasis. Additionally, the Olympus EndoClip is a semi-reusable device, causing the performance of the device to degrade with use.

SUMMARY OF THE INVENTION

The present invention provides medical devices for causing the hemostasis of blood vessels located along the gastrointestinal tract. The goal of the invention is to give the endoscopist a technique and device which: 1) has a success rate in line with the surgical option; 2) is easier to set-up than the Olympus EndoClip; and 3) is easier to deploy than the Olympus EndoClip. The design intent is to eliminate surgery and its associated mortality and morbidity.

The medical devices of the present invention include: a compression clip used to cause hemostasis of blood vessels and a mechanism for deploying the clip that includes an arrangement for closing the clip and for reversing the closing process to reopen the clip after closure has begun. Embodiments of the invention may include a lock arrangement for locking the clip closed; a control wire connected to the clip and able to be disconnected from the clip; an axially rigid sheath enclosing the control wire and communicating a compressive force opposing a tensile force of the control wire; a handle connected to the axially rigid sheath; and/or a trigger enclosed within the handle and engaging the control wire to close and lock the clip and to uncouple the control wire from the clip.

There are several key advantages of the invention disclosed here over existing devices. The device's ability to repeatedly open and close the clip until the desired tissue pinching is accomplished will lead to a quicker procedure, requiring less clips to be deployed, with a higher success rate. In particular embodiments, this higher success rate will be improved even more due to the device's ability to be easily rotated so that the clip legs can be adjusted relative to the bleeding vessel. In particular embodiments, the time required to perform the overall procedure will also be further reduced due to the fact that the device is completely set up, with the clip already attached to the delivery device, unlike the competitive device. A more robust delivery device may allow a larger, stronger clip to be delivered. Combinations of these features will provide for a device that is easier to use.

Another advantage inherent to particular embodiments of this design is the feature of being completely disposable. The competitive device, the Olympus Endoclip, uses a "semi-reusable" delivery device, capable of firing several clips before it fails. This causes the device's functionality to degrade over the course of its use, until it is no longer able to deploy a clip. The competitive delivery device must be loaded manually, which is cumbersome to the operator and time-consuming, especially in the context of an unplanned emergency procedure. The "single-use" (disposable) embodiments of the invention disclosed here would function the same with each clip, in each procedure.

BRIEF DESCRIPTION OF THE DRAWINGS

FIG. 8F shows enlarged partial side views of various embodiments of clip leg shapes available for use in the medical device of the present invention.

FIG. 8G shows enlarged partial end views of various embodiments of clip leg shapes available for use in the medical device of the present invention.

FIG. 11 is an enlarged partial view of another embodiment of the medical device of the present invention.

FIG. 14A is an enlarged partial view of another embodiment of the medical device of the present invention.

FIG. 14B is an enlarged partial side view of the embodiment of FIG. 14A.

FIG. 14C is an enlarged partial view of the distal end of the medical device of the embodiment of FIG. 14A after the clip has been released.

FIG. 18A is an enlarged view of clip legs of another embodiment of the medical device of the present invention.

FIG. 18B is an enlarged partial view of an embodiment of the medical device of the present invention using the clip legs of FIG. 18A.

FIG. 18C is an enlarged partial view of the embodiment of FIG. 18B, showing the clip in a closed position.

FIG. 18D is an enlarged edge view of the clip of the embodiment of FIG. 18B.

FIG. 18E is an enlarged partial end view of the embodiment of FIG. 18B.

FIG. 18F is an enlarged partial side view of the embodiment of FIG. 18B.

FIG. 20A is an enlarged partial end view of another embodiment of the medical device of the present invention.

FIG. 20B is an enlarged partial side view of the embodiment of FIG. 20A.

FIG. 20C is a side-by-side comparison of two parts of the embodiment of FIG. 20A.

DETAILED DESCRIPTION

Figure 1:
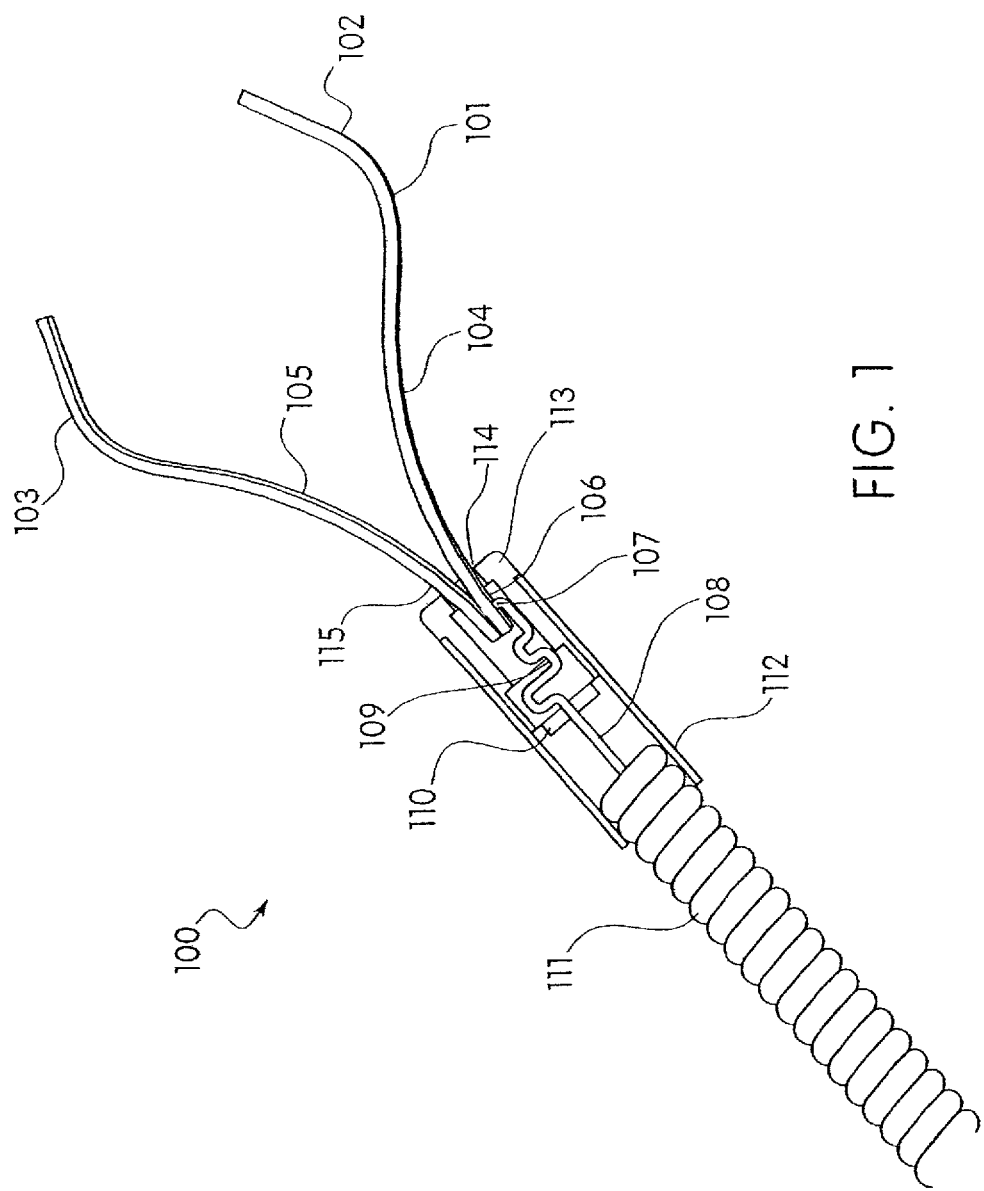
FIG. 1 is an enlarged partial view of a first embodiment of the medical device of the present invention.

In a first embodiment of the invention as shown in FIG. 1, medical device 100 includes a clip 101 having first clip leg 102 and second clip leg 103. Clip leg 102 has at least one lock hole 104 therein of any suitable shape (e.g. circular, rectangular, square, etc.). Likewise, clip leg 103 has at least one lock hole 105 therein of any suitable shape. Clip 101 is further characterized by a cut-out 106 on the proximal end. J-hook 107 is inserted into cut-out 106. J-hook 107 is formed on the distal terminal end of control wire 108. A retainer release 109 is formed by bends in the control wire 108, the bends formed proximally from the j-hook 107. The control wire 108 is enclosed within sheath 111 proximally from the retainer release 109. Retainer 110 is coupled to control wire 108 and engages lock sleeve 113.

Retainer release 109 acts to disengage retainer 110 from lock sleeve 113 when a tensile force applied to control wire 108 is sufficient to cause such disengagement.

An outer sleeve 112 is connected on the distal side of sheath 111, and lock sleeve 113 is connected to a distal side of outer sleeve 112. Lock sleeve 113 incorporates lock pawl 114, which engages lock hole 104 in clip leg 102, and lock pawl 115, which engages lock hole 105 in clip leg 103.

The clip 101 is a deformable, multi-legged, grasping device attached to the distal portion of a flexible shaft (the sheath 111) via a frangible link (the j-hook 107). The flexible shaft is connected at its proximal end to a handle (FIG. 7), the handle analogous to biopsy forceps. A semi-rigid wire (the control wire 108), which is routed from the handle to the clip 101, acts as a means of actuating the clip 101 between the open and closed position. The clip 101 can be actuated between the open and closed position multiple times as long as the lock holes 104 and 105 do not become engaged with the lock pawls 114 and 115 in the lock sleeve 113. Once the operator decides the clip 101 should be permanently deployed, the handle can be fully actuated, which causes the retainer release 109 to pull the retainer 110 free from the outer sleeve 112 and lock sleeve 113. After the retainer 110 is released, increasing force will begin straightening the j-hook 107. The j-hook 107 is then pulled from the cut-out 106 on the proximal side of clip 101. At this point, the retainer 110 and control wire 108 are no longer attached to the distal portion of the device (the clip 101 and lock sleeve 113) and the delivery device (e.g. an endoscope, not shown) can be removed while leaving the clip 101 (with lock sleeve 113) in place.

The sheath 111 serves three key functions in this embodiment. In its primary function it acts as a housing for the control wire 108. In this function the sheath 111 supplies a resistive, compressive force opposite the tensile force applied to the control wire 108, via the handle, as the lever (FIG. 7) in the handle is moved to close the clip 101. The forces reverse when the lever is moved in the opposite direction, and the control wire 108 is compressed to push the clip 101 forward. In this function, the combination of control wire 108 and sheath 111 act as a simple push-pull, cable actuation mechanism.

In the secondary function of sheath 111, it acts as a means by which the clip 101 can be easily rotated. Ideally this rotation would be of a ratio of 1:1. In other words, one complete rotation of the sheath 111 at the proximal end would translate to one complete rotation of the clip 101. This rotation however, depends on several factors. The relationship of the outside diameter of sheath 111 to the inside diameter of the working channel (not shown) of the endoscope (not shown), is one factor. Another factor is the amount of friction between the sheath 111 and the working channel caused by the path of the endoscope in the anatomy. Because these factors vary from endoscope to endoscope, and patient to patient, the rotation ratio will not always be the same. This ease of rotation is a key function and benefit of this embodiment in that it allows relatively precise orientation of the clip 101 to the vessel. Depending on the exact construction of the sheath 111, and the other factors just listed, rotation of the device may be different in one direction of rotation versus the other direction. By taking advantage of the mechanical properties of the sheath 111, this embodiment accomplishes rotation without the need for additional handle components. Eliminating the need for such components will: reduce the overall cost of the device; simplify how the device is operated; and make rotation more repeatable. In turn, all of these benefits will make for a faster procedure with a higher success rate.

The sheath 111 accomplishes a high rotation ratio by using a spiral wound, multiple-wire, stainless steel, flexible shaft, with an outside diameter of slightly less than the inside diameter of the working channel of the endoscope. Because the sheath 111 is made of a multiple-wire configuration, it is soft and bendable, yet rigid in rotation. In other words, the sheath 111 is flexible enough to be manipulated through a flexible endoscope, but has a very low angle of twist about its central axis.

In the third function of the sheath 111, it acts as a component of the mechanism by which the clip 101 is released. The outer sleeve 112, which is rigidly attached to the sheath 111 by methods known in the prior art (e.g. adhesives, welding, swaging, etc.), is made of a rigid tube, with two retainer cut-outs (not shown), situated 180° apart from each other. These retainer cut-outs house the two tabs 118, 119 (FIG. 6) of the retainer 110. As the control wire 108 is actuated, drawing the clip 101 back into the lock sleeve 113, the retainer release 109 forces the retainer 110 to be disengaged from the outer sleeve 112.

Figure 2:
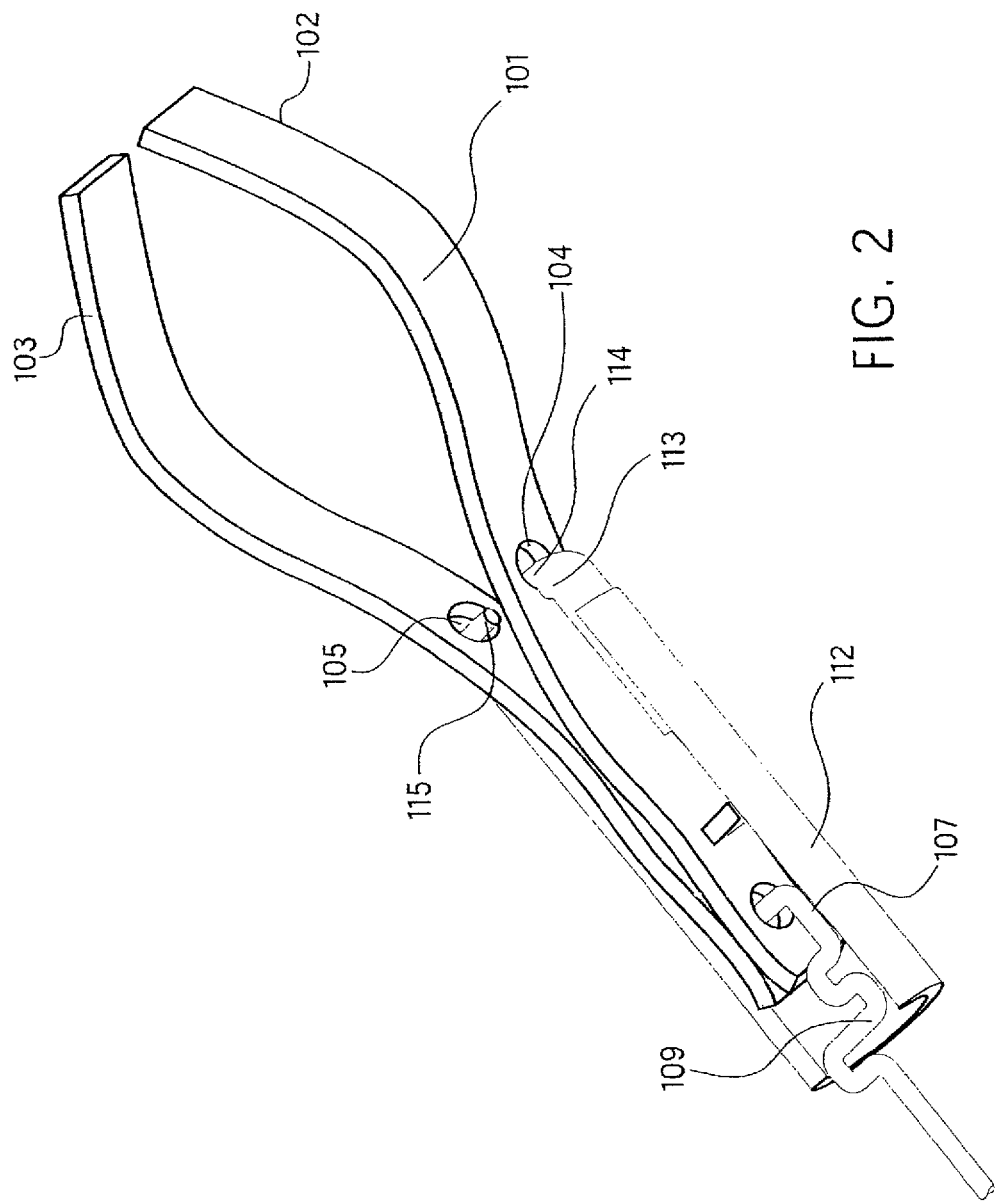
FIG. 2 is an enlarged partial view of the distal end of the embodiment of FIG. 1.

FIG. 2 shows the clip 101 in the closed position but prior to release of the j-hook 107. In the closed, locked position shown in FIG. 2, lock hole 104 of clip leg 102 is engaged by lock pawl 114, and lock hole 105 of clip leg 103 is engaged by lock pawl 115. The fit between the lock sleeve 113 and outer sleeve 112 is such that the lock sleeve 113 (and therefore the clip 101) will easily release from the outer sleeve 112 once the j-hook 107 has been straightened and the retainer disengaged from the outer sleeve 112.

Figure 3:
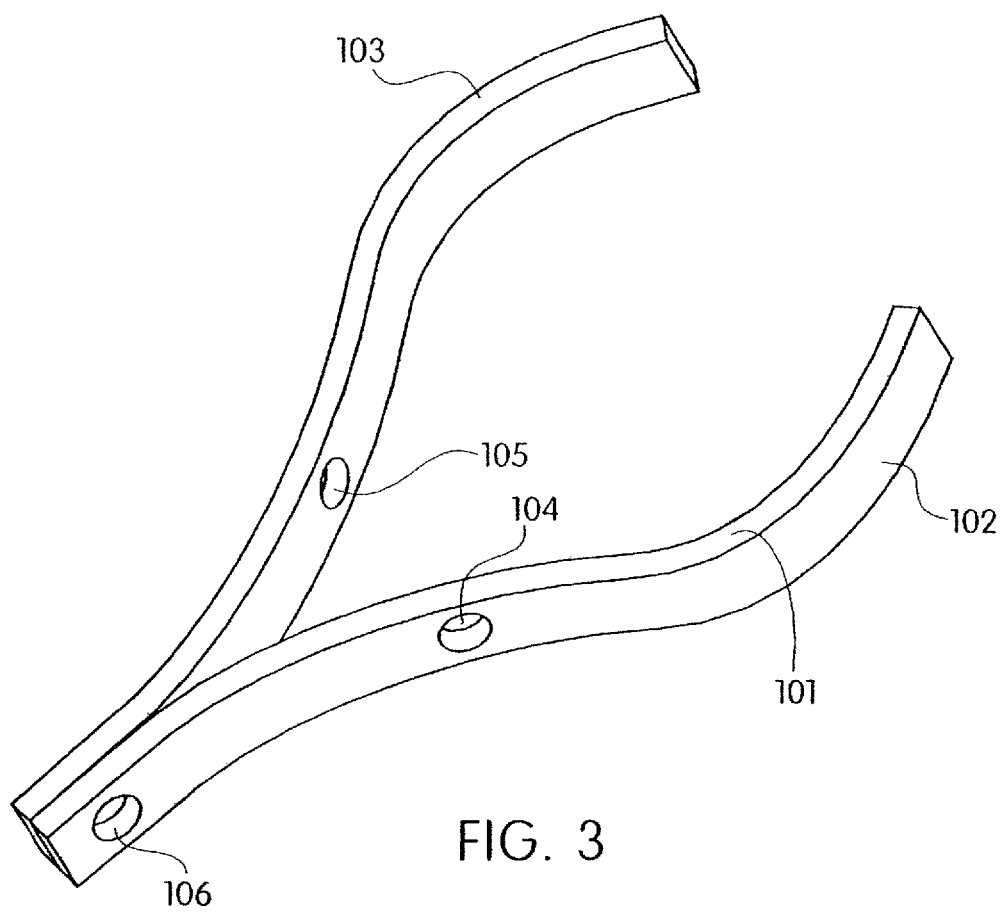
FIG. 3 is an enlarged view of the clip of the embodiment of FIG. 1.

The clip 101, shown in FIG. 3, is manufactured of a single piece of stainless steel, or any suitable biocompatible material, and is bent into a two-legged geometry. The clip legs 102 and 103 have a rectangular cross section of approximately 0.06 inches by 0.01 inches and are approximately 0.50 inches in length. The profile of the legs serves three purposes: first, the distal portion grasps the tissue during the procedure; second, the distal portion acts as the compression mechanism to hold the clip in place after deployment; and third, the profile between the distal grasping portion and the proximal end will interface with the lock pawls (not shown), via lock hole 104 in clip leg 102 and lock hole 105 in clip leg 103. The interface between the lock holes and the lock pawls creates the mechanical lock that will keep the clip 101 closed after deployment. The proximal end of the clip 101 is formed with a cut-out 106 into which the j-hook (FIG. 2) is attached.

Figure 4:
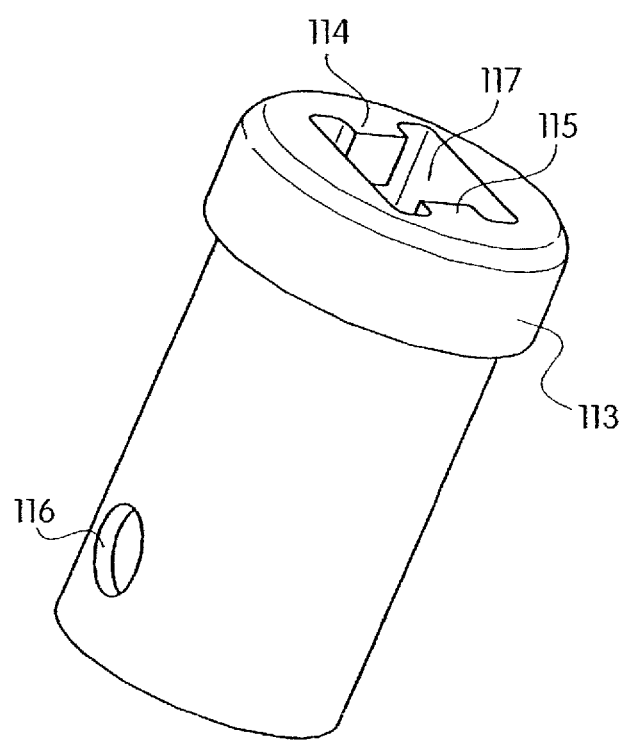
FIG. 4 is an enlarged view of the lock sleeve of the embodiment of FIG. 1.
Figure 6:
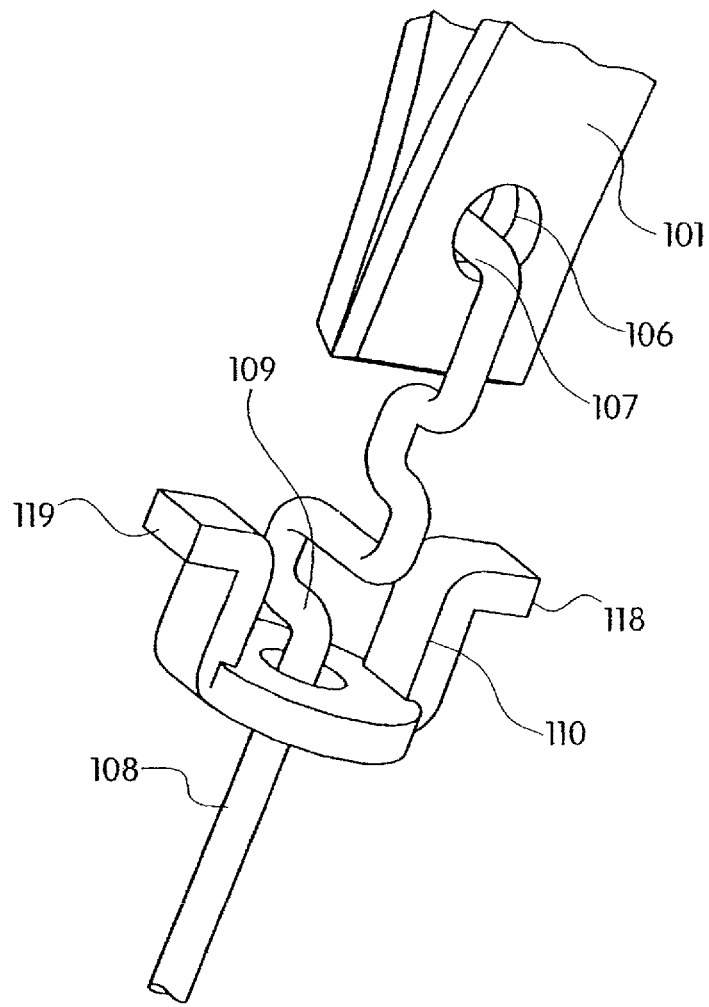
FIG. 6 is an enlarged partial view of the control wire, retainer, and clip of the embodiment of FIG. 1.

The lock sleeve 113 shown in FIG. 4 consists of a tubular proximal section, which fits into the distal end of the outer sleeve 112. Retainer hole 116 and opposite retainer hole (not shown) in the lock sleeve 113 receive the retainer tabs 118, 119 (FIG. 6). The distal end of the lock sleeve 113 has a lock sleeve cut-out 117 slightly larger than the cross section of the clip legs (FIG. 3). As the clip leg are pulled through cut-out 117, the clip legs are compressed toward each other, thus compressing the tissue (not shown) situated between the clip legs. The cut-out 117 has lock pawls 114 and 115, which align with the two lock holes (FIG. 3) in the clip legs. After the desired tissue purchase has been acquired, the clip can be pulled back far enough to engage the lock pawls 114 and 115 into the two lock holes.

Figure 5:
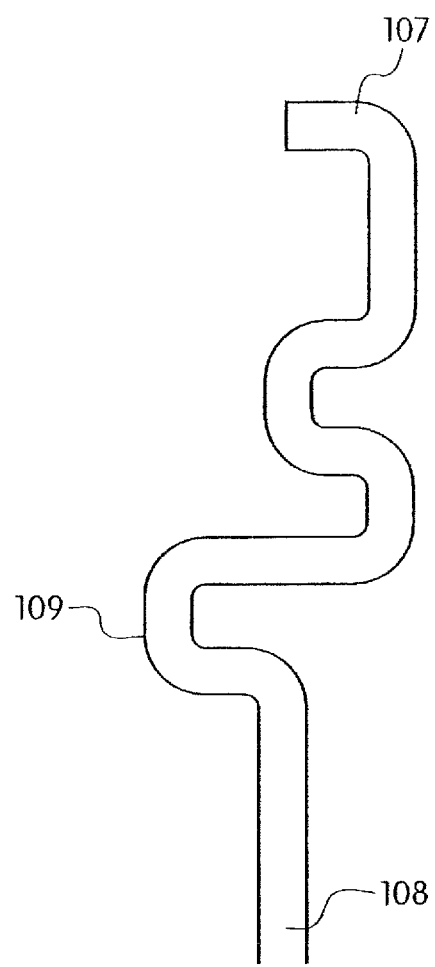
FIG. 5 is an enlarged view of the j-hook of the embodiment of FIG. 1.

Forming the end of the control wire 108 into a j-hook 107 makes a frangible link shown in FIG. 5. This relatively simple configuration eliminates extraneous components that take up space and complicate the assembly. The control wire 108 is bent such that it wraps around the proximal end of the clip (FIG. 3), through a cut-out (FIG. 3). Another bend in the wire, proximal to the j-hook 107, acts as a retainer release 109. The retainer release 109 operates to release the retainer 110 (FIG. 6) from the lock sleeve 113 (FIG. 4). As the control wire 108 is actuated and the clip is locked into the lock sleeve, the retainer release 109 pulls the retainer 110 back, disengaging the retainer tabs 118, 119 from the two retainer holes 116 (FIG. 4) in which the retainer normally resides. After this disengagement is complete, the j-hook 107 is then straightened by force, in turn releasing the clip. The j-hook 107 is able to deform to a straightened position (i.e. release) at a predetermined tensile load, which is slightly greater than the load required to grasp the tissue (not shown), compress the tissue, and engage the lock pawls (FIG. 4) in the lock holes (FIG. 3).

The control wire 108 shown in FIG. 6 is a simple stainless steel wire used to actuate the clip 101 via a handle (FIG. 7), at the proximal end of the sheath (FIG. 1). In this embodiment of the invention, the frangible link (the j-hook 107) is formed in the distal end of the control wire 108 as a one-piece design. The proximal end of the control wire 108 is terminated inside the handle. The control wire 108 also has the retainer release 109 formed in it, behind the j-hook 107. The retainer release 109 causes the outer sleeve (FIG. 1) to disengage from the retainer 110. This is done sequentially, after the lock holes (FIG. 3) in the clip 101 have engaged the lock sleeve (FIG. 4). After the lock holes engage the lock sleeve, tensile force applied to control wire 108 first straightens j-hook 107 so that j-hook 107 releases from cut-out 106, then retainer release 109 engages and deforms retainer 110 so that retainer tabs 118 and 119 disengage from the outer sleeve (FIG. 1) and the lock sleeve (FIG. 4). Alternatively, retainer release 109 could engage and deform retainer 110 before j-hook 106 straightens and disengages from cut-out 106.

Figure 7:
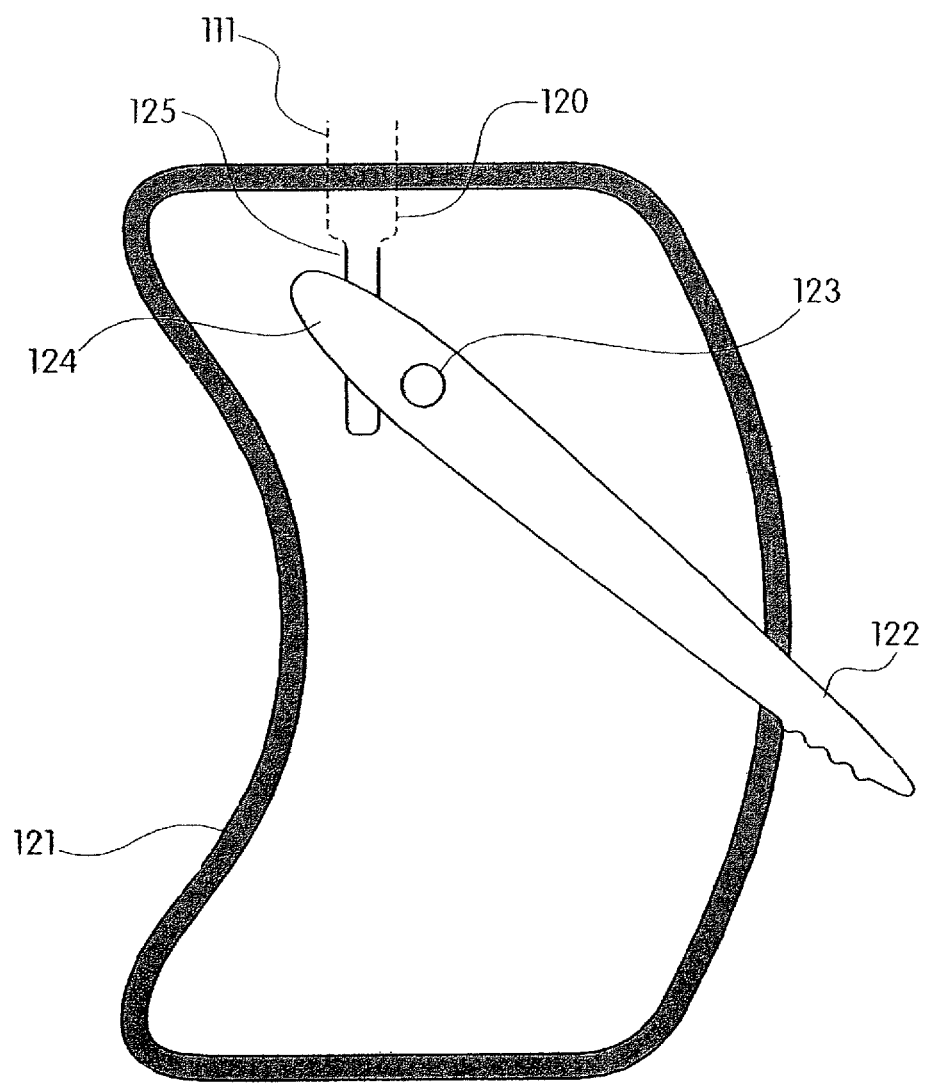
FIG. 7 is an enlarged partial view of the handle of the embodiment of FIG. 1.

The handle shown in FIG. 7 is attached to the proximal end of the sheath 111 at a sheath-handle attachment point 120. The handle configuration is unlike a handle found on conventional endoscopic forceps known in the prior art. The handle provides a mechanism by which the amount of linear actuation required in the handle body 121 is greater than that which is translated to the tip of the device (FIG. 1). In other words, actuation of the activator or handle lever 122 of 1.00 inch in turn may only move the clip (FIG. 3) by 0.10 inch. This feature allows for a more tactile feel when placing the clip on the vessel (not shown). In effect, very subtle amounts of movement in the clip can be accomplished by more exaggerated, less precise movements of the operator's hand. This is accomplished because the activator or lever 122 pivots about a pivot point 123 that is close to the attachment point 124 of the control wire 125.

Figure 8A:
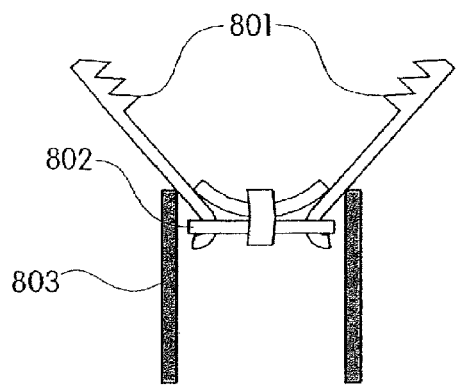
FIG. 8A is an enlarged partial view of the distal end of another embodiment of the medical device of the present invention.
Figure 8B:
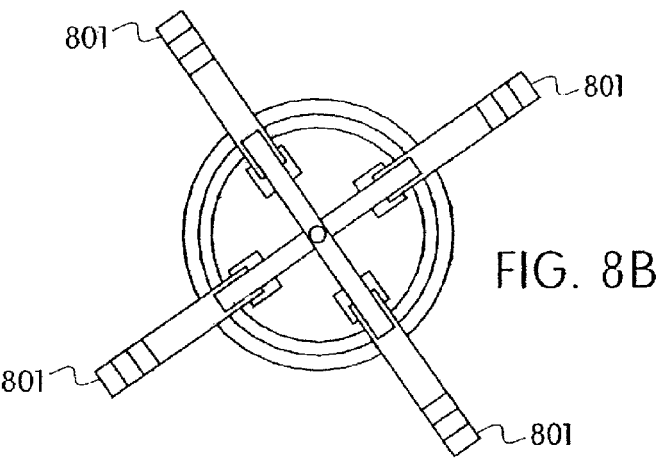
FIG. 8B is an enlarged partial end view of the embodiment of FIG. 8A.
Figure 8C:
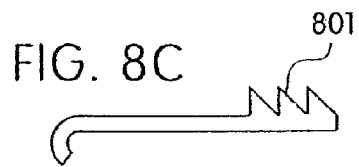
FIG. 8C is an enlarged partial view of a clip leg of the embodiment of FIG. 8A.
Figure 8D:
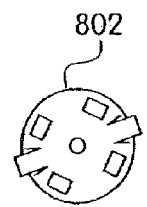
FIG. 8D is an enlarged partial view of a clip locking mechanism of the embodiment of FIG. 8A.
Figure 8E:
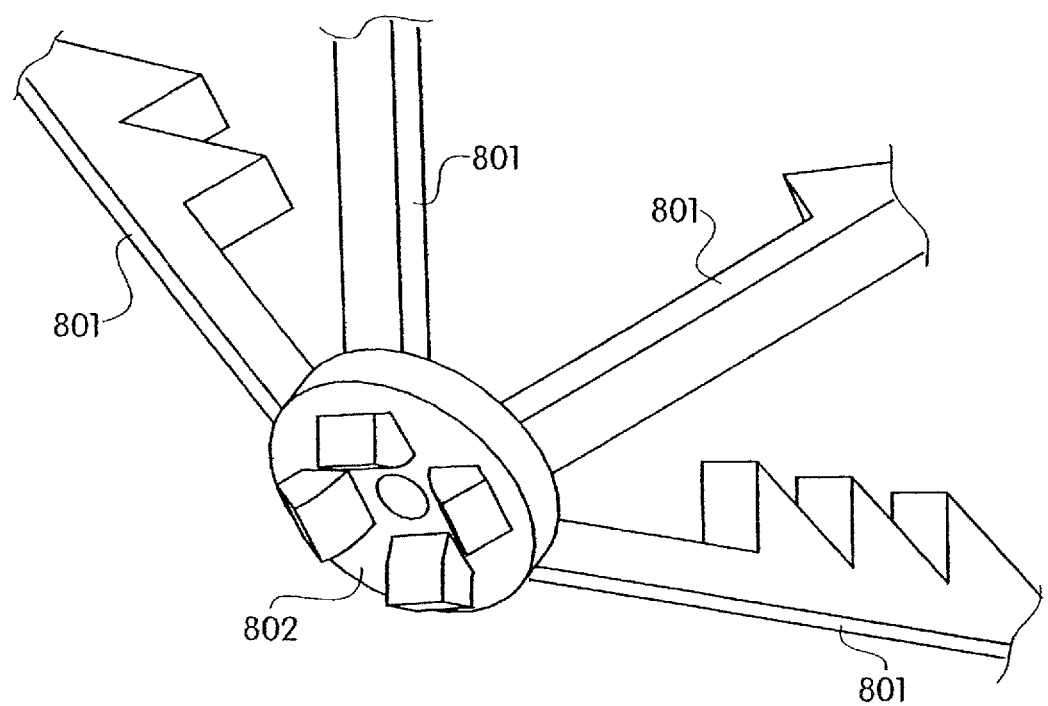
FIG. 8E is an enlarged partial view of a clip locking mechanism and clip legs of the embodiment of FIG. 8A.

An alternative embodiment of the device may be made up of clips with more than two legs. FIGS. 8A through 8E show a clip with four legs. FIG. 8A shows a view from the side, showing clip legs 801. This embodiment could be actuated and released in the same way the previous embodiment is activated and released, through a clip locking mechanism 802. The use of a control wire (not shown) would actuate the multiple-legged clip in and out of an outer sleeve 803 until such time that the operator desires to release the clip. Alternatively, actuation of the control wire might move the outer sleeve 803 in and out over the multiple-legged clip to open and close the clip legs 801, until such time that the operator desires to release the clip. FIG. 8B shows the four-legged clip of FIG. 8A from the perspective of the targeted tissue looking proximally. The four clip legs 801 are shown in an open position and are situated at 90° from each other. FIG. 8C shows a profile view of a single clip leg 801. FIG. 8D shows a view along the axis of clip locking mechanism 802. FIG. 8E shows another view of a four-legged clip with clip legs 801 and clip locking mechanism 802.

FIG. 8F shows alternative side profiles of the clip geometry. Use of such geometries in a clip with two or more legs allows for improved grasping ability in different situations. Given the large variation in tissue thickness and tissue strength, it is likely that different clip profiles would excel in different procedures. FIG. 8G shows alternative end profiles of the clip geometry. As with the varying side profiles, different end profiles would provide a broader range of grasping capabilities.

Figure 9B:
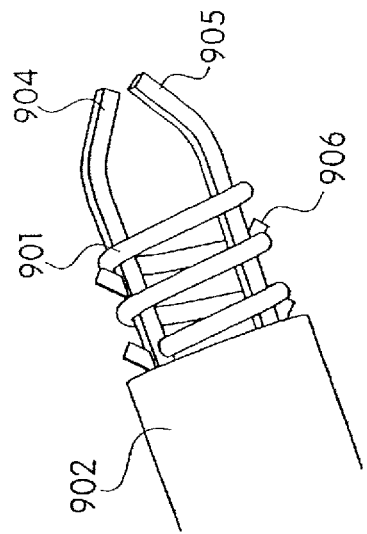
FIG. 9B is an enlarged partial view of the embodiment of FIG. 9A being deployed.
Figure 9A:
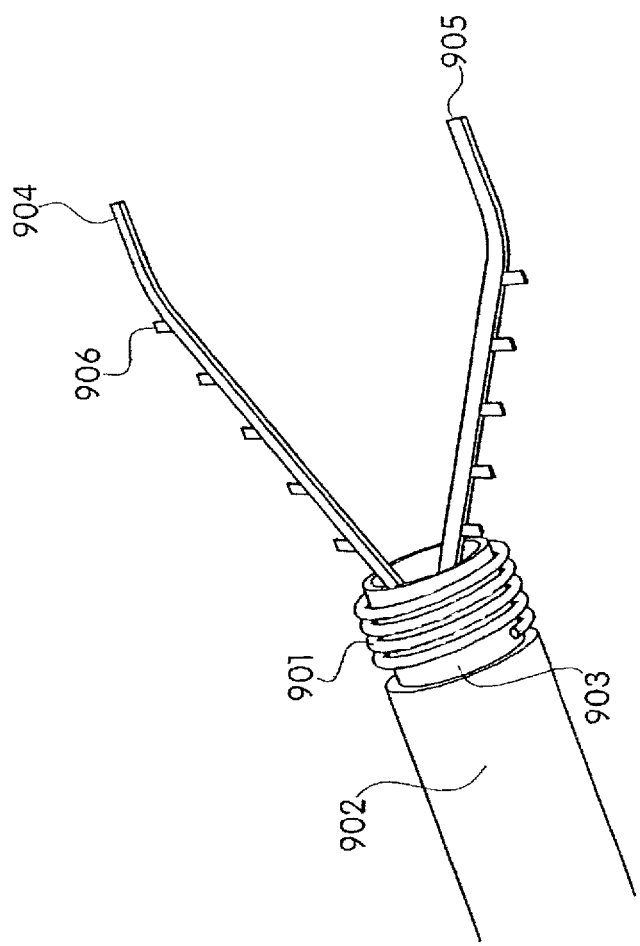
FIG. 9A is an enlarged partial view of the distal end of another embodiment of the medical device of the present invention.

FIGS. 9A and 9B illustrate an alternative embodiment of the device using a different method to lock the clip in the closed position. This alternative method uses an expanded coil spring 901 released over the outside of the clip legs 904 and 905 to lock the clip legs 904 and 905 closed. FIG. 9A shows this embodiment in a predeployment state. FIG. 9A shows a stretched coil spring 901, twisted to a diameter larger than that of the relaxed state of coil spring 901. Stretched coil spring 901 is placed over a rigid tube 903 at the distal end of the clip device. Within this rigid tube 903, the clip legs 904 and 905 are free to move in and out (in a manner similar to the manner described for the previous embodiments), between the opened and closed position via a control wire (not shown). When the desired clip location has been achieved, the sheath 902 is used to push the coil spring 901 off of the rigid tube 903, onto the clip legs 904 and 905, as shown in FIG. 9B. The inward radial forces present in the recovered coil spring 901 act to keep the clip legs 904 and 905 compressed.

Figure 10B:
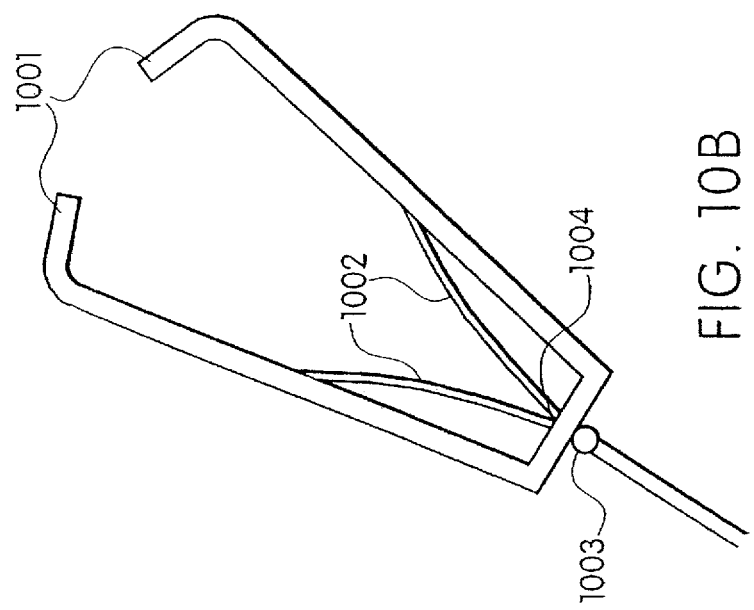
FIG. 10B is an enlarged partial view of the embodiment of FIG. 10A being deployed.
Figure 10A:
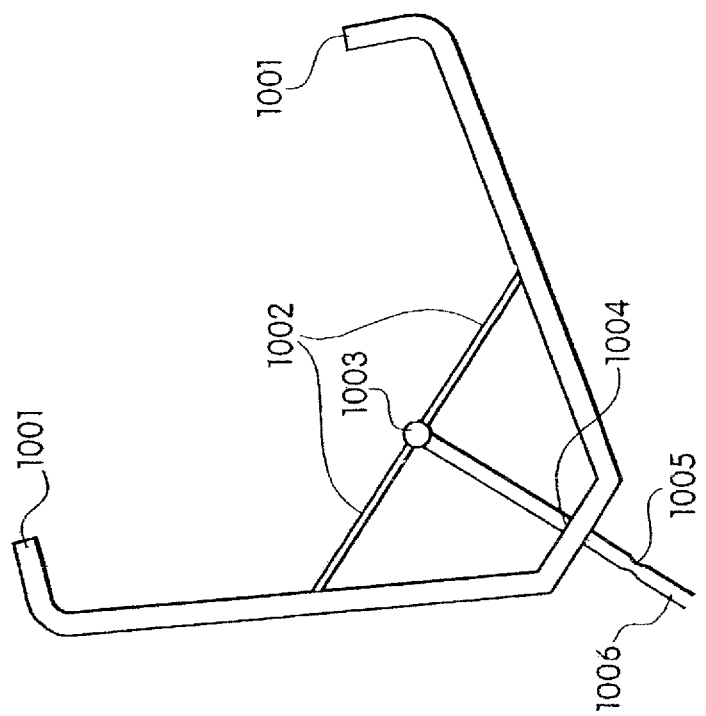
FIG. 10A is an enlarged partial view of another embodiment of the medical device of the present invention.

FIGS. 10A and 10B illustrate another alternative embodiment. In this embodiment, a flexible linkage 1002 and pill 1003 are used to lock the clip legs 1001. In this embodiment the clip legs 1001 are actuated via a control wire 1006, as described in previous embodiments. However, in this embodiment, the clip legs are not closed by pulling the clip legs 1001 through some feature smaller than the open clip. Instead the clip legs 1001 are closed by drawing the two flexible links 1002 proximally, in the direction of the control wire 1006, while a compressive force is applied to the base of the clip legs 1001 by a rigid sheath (not shown). This in turn pulls the legs of the clip toward each other. FIG. 10A shows the clip legs 1001 in an open position. FIG. 10B shows the clip legs in a closed position. The clip legs 1001 are locked in a closed position when the pill 1003, located at the center of the flexible linkage 1002, is drawn through a one way hole 1004 in the center of the clip legs 1001. The one way hole 1004 is tapered, with a diameter slightly larger than the diameter of the pill 1003 on its distal side and a diameter smaller than the diameter of the pill 1003 on its proximal side. The pill stretches the material around the hole 1004 as it passes through moving proximally. Alternatively, the pill 1003 itself can be made of an elastic material and would deform slightly while passing proximally through hole 1004. This funneling effect of the pill 1003 through the hole 1004 only allows the pill 1003 to easily pass through in the locking direction. This locking action is maintained after the clip is released by positioning the frangible link 1005 in a proximal direction on control wire 1006 from the pill 1003, thus maintaining tissue compression. In this embodiment the frangible link 1005 is a taper in control wire 1006, enabling the link to be broken at a specific position (proximal from the pill 1003) with a predetermined tensile load.

One alternative to the j-hook type frangible link previously described is shown in FIG. 11. This embodiment uses a threaded fitting that is a combination of a male thread 1103 and a female hub 1102 to attach the control wire (not shown) to the clip 1001. The clip 1001 can be actuated from the opened position (not shown) to the closed position (shown) as described in previous embodiments. In this embodiment, the lock sleeve 1105 is shorter and engages dimples 1106. After the lesion (not shown) is properly targeted, the clip 1101 can be released. The clip 1101 is released when a predetermined tensile load is applied to the male thread 1103, in a similar fashion to the predetermined tensile load applied to straighten the j-hook. This force causes the male thread 1103 to detach from the female hub 1102. The female hub 1102 may be constructed of a spiral wound wire component with a pitch equal to the thread pitch formed to make the male thread 1103. The fit of the threaded components is such that the predetermined force will overcome the engaged threads of the male thread 1103 and the female hub 1102, causing them to separate, or "strip" away from one another.

Figure 12B:
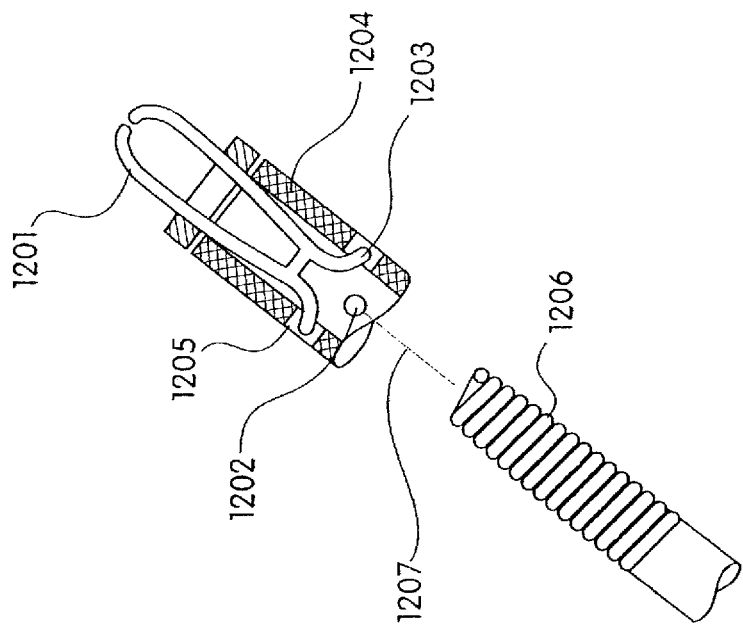
FIG. 12B is an enlarged partial view of the embodiment of FIG. 12A showing the clip in a closed position.
Figure 12A:
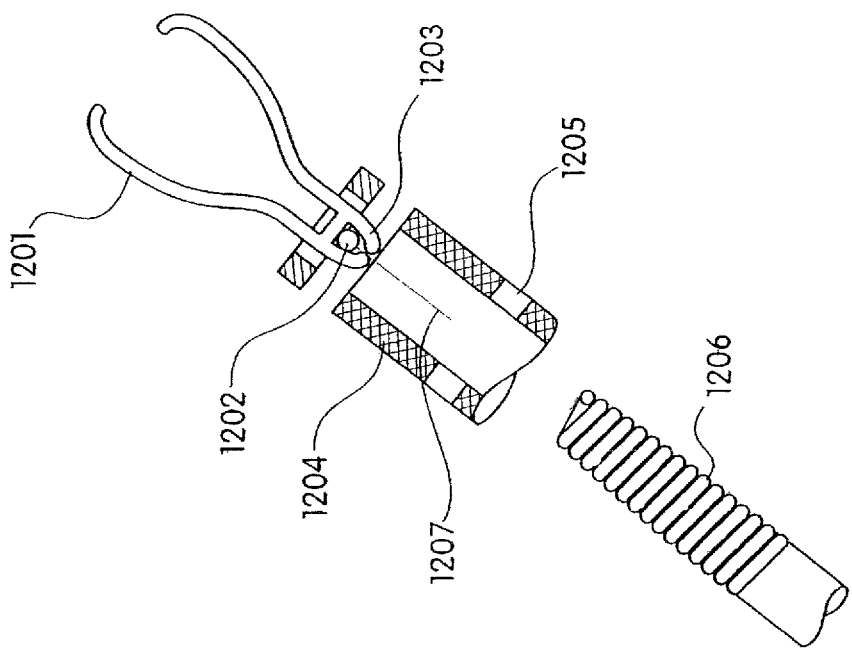
FIG. 12A is an enlarged partial view of another embodiment of the medical device of the present invention showing the clip in an open position.

Another alternative to the j-hook type frangible link is shown in FIGS. 12A and 12B. This embodiment uses a ball 1202 fitting into a socket, where the socket is defined by socket tabs 1203, to attach the control wire 1207 to the clip 1201. An outer sleeve 1204 is attached by way of a breakaway connection (not shown) to the sheath 1206. This breakaway connection may be a light interference fit, or a light adhesive joint. The breakaway connection must be weak enough that when the sheath 1206 is pulled back through the working channel (not shown) of the endoscope (not shown), the outer sleeve 1204 will release with the clip 1201. The clip 1201 is released when the socket tabs 1203 at the proximal end of the clip 1201 are aligned with cut-outs 1205 in the outer sleeve 1204. These cut-outs 1205 act as a relief area into which the socket tabs 1203 can be deformed when a predetermined tensile load is applied to them via the ball 1202 formed on the end of the control wire 1207. The outer sleeve 1204 is released with clip 1201 so that the clip 1201 remains locked after deployment.

Figure 13A:
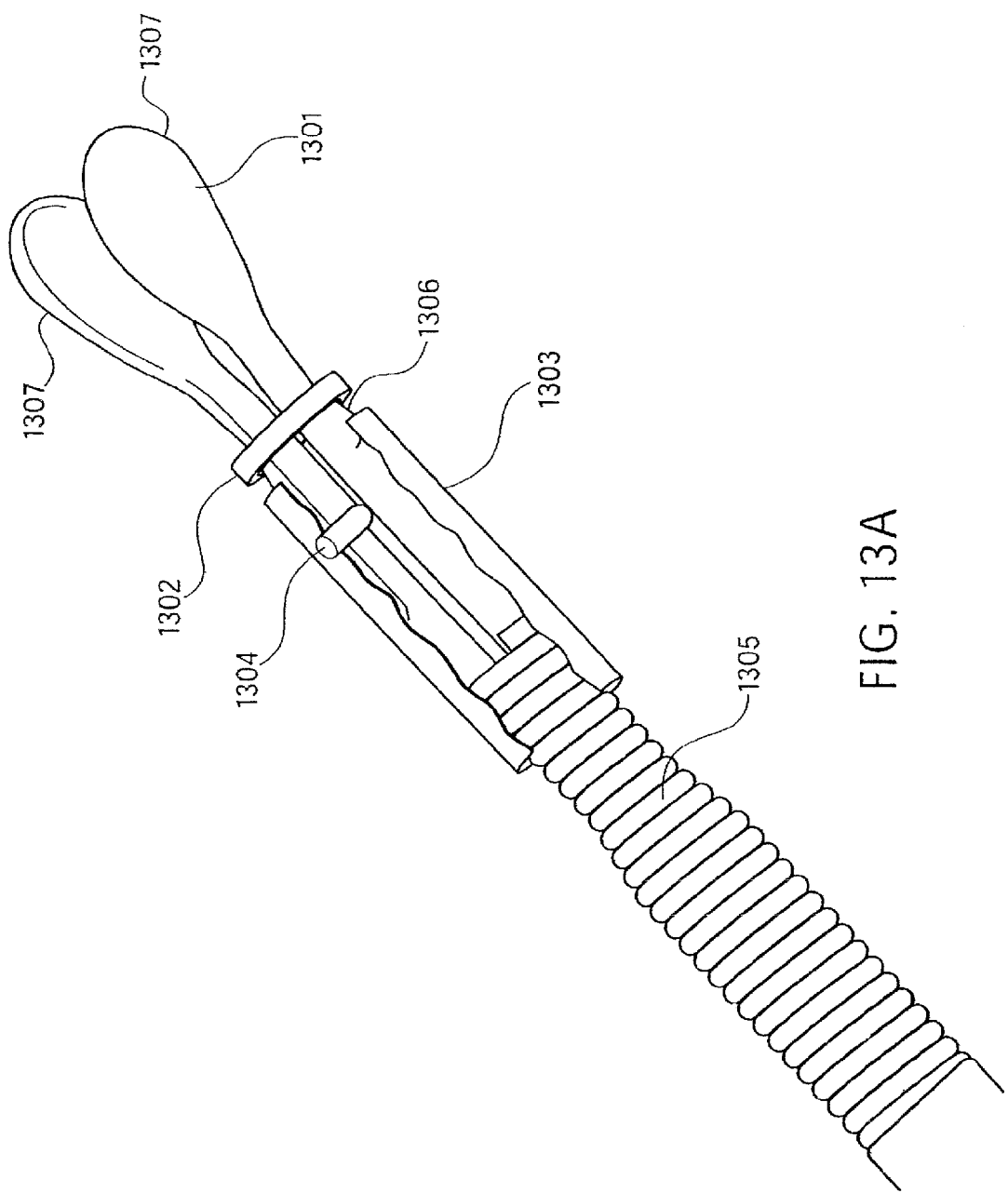
FIG. 13A is an enlarged partial view of another embodiment of the medical device of the present invention showing the clip in a closed position prior to disconnecting the clip.
Figure 13B:
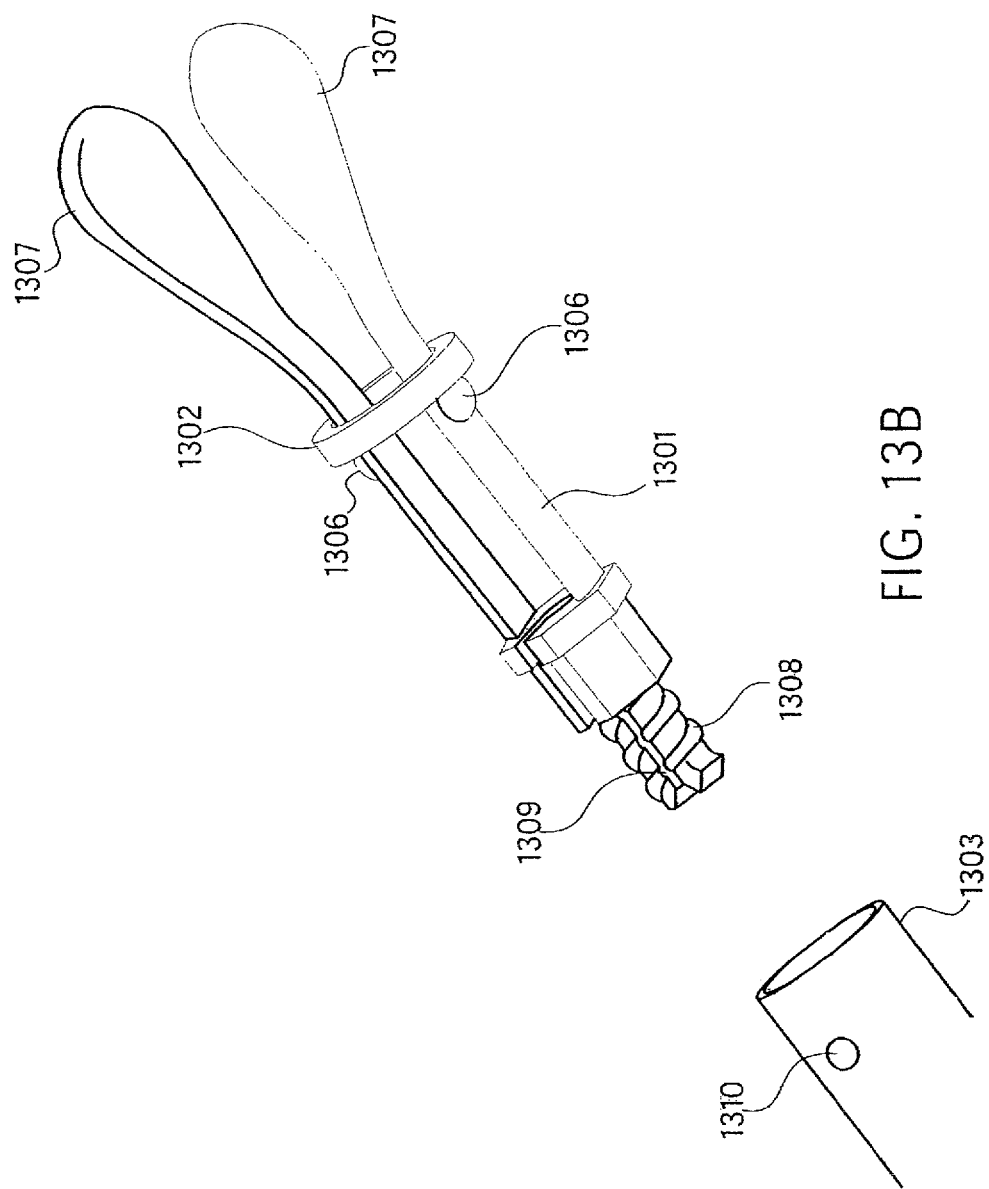
FIG. 13B is an enlarged partial view of the distal end of the embodiment of FIG. 13A showing the clip in a closed position after disconnecting the clip.
Figure 13C:
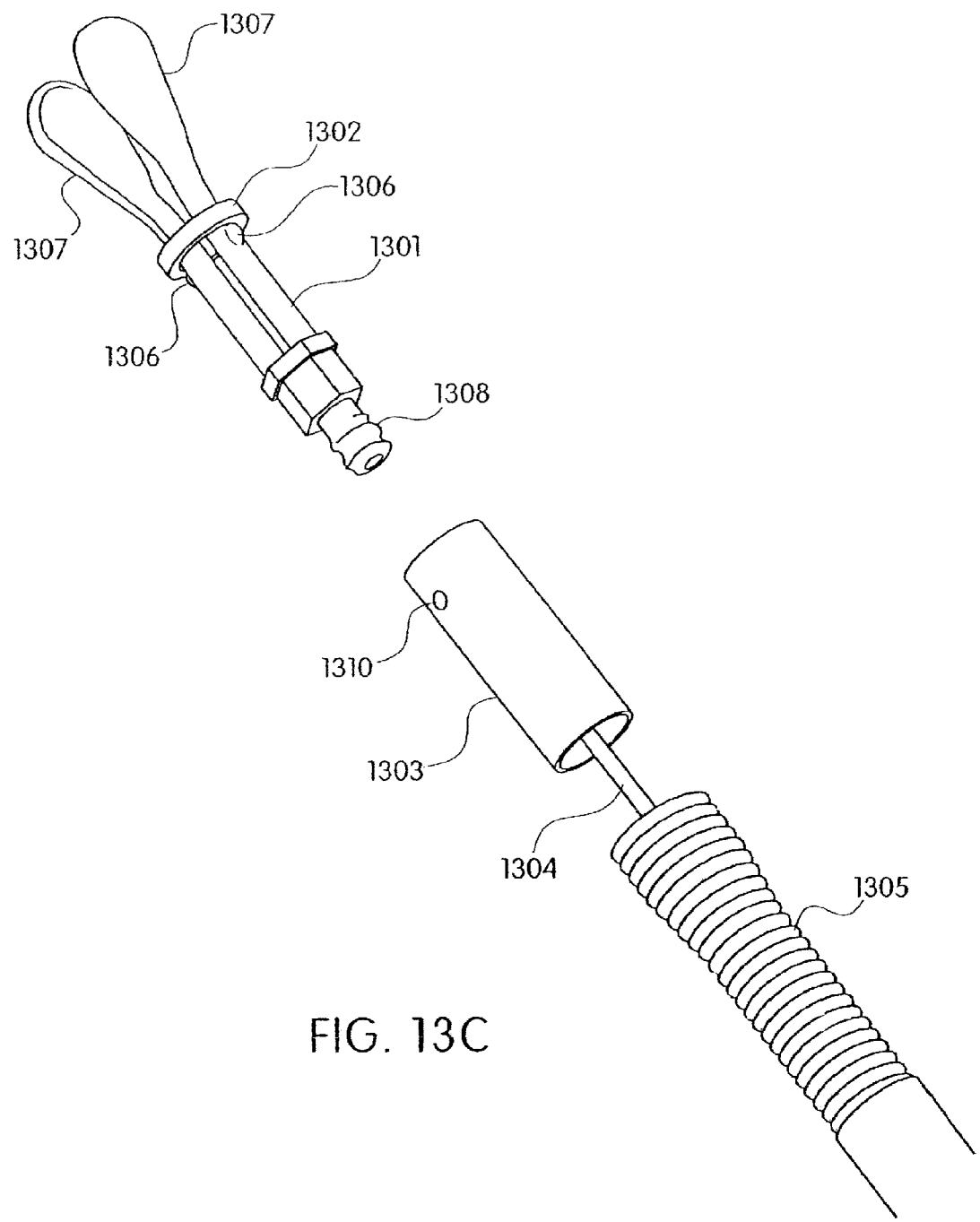
FIG. 13C is an enlarged partial view of the embodiment of FIG. 13A showing the clip in a closed position after disconnecting the clip.

Another alternative to the j-hook type frangible link is shown in FIGS. 13A, 13B and 13C. All the figures show the clip 1301 in a closed and locked state. FIG. 13A shows the clip 1301 in a closed position but before it is released and shows a portion of outer sleeve 1303 cut away to show the internal workings of the clip mechanism. FIGS. 13B and 13C show the clip 1301 after being released. In this embodiment, the actuation is still performed via a control wire 1304, however the direction of action is reversed. As the control wire 1304 is pushed forward, the clip 1301 is closed by the advancement of outer sleeve 1303 and lock ring 1302 over the clip legs. The locking sleeve 1302 and clip geometry, including dimples 1306, is the same as that explained in the embodiment of FIG. 11.

A difference between the embodiment shown in FIGS. 13A, 13B and 13C and the prior embodiments is the mechanism by which the clip 1301 is released from the rest of the device. An interference fit between the outer sleeve 1303, sheath 1305, and male threaded hub 1308 is created when the device is assembled. The distal end of the sheath 1305, in its manufactured (but unassembled) state, has an outside diameter greater than the inside diameter of the outer sleeve 1303. When the outer sleeve 1303 and sheath 1305 are assembled together part of the interference fit is created. The distal end of the sheath 1305, again in its manufactured (unassembled) state, has an inside diameter greater than the diameter of the male threaded hub 1308. During assembly, as the distal end of the sheath 1305 is compressed to fit inside the outer sleeve 1303, it is compressed down onto the male threaded hub 1308 to create a sandwich of the sheath 1305 between the male threaded hub 1308 on the inside and the outer sleeve 1303 on the outside. During the medical procedure, at the time the operator wishes to release the clip 1301, this interference fit is overcome. The interference fit is overcome by advancing the outer sleeve 1303 so far forward, by creating a compressive force in the control wire 1304 in opposition to a tensile force on the sheath 1305, that the outer sleeve 1303 is no longer in contact with the distal end of the sheath 1305.

The outer sleeve 1303 and the control wire 1304 serve two purposes in this embodiment. The outer sleeve 1303 and the control wire 1304 supply the closing force to the clip 1301. In FIGS. 13A, 13B, and 13C, a lock ring 1302 is used to maintain the closing force on the clip legs 1307. The outer sleeve 1303 and the control wire 1304 also act as key components of the release mechanism. As previously described, once the outer sleeve 1303 is moved to its forward-most position, the end of the sheath 1305 is no longer contained within the outer sleeve 1303, and is free to separate from the male threaded hub 1308. The sheath 1305 is free to release because of the manner in which the distal end of the sheath 1305 is manufactured/assembled.

When the outer sleeve 1303 is advanced forward, allowing the distal end of the sheath 1305 to be free, the distal end of the sheath 1305 expands to its original, manufactured state. This allows the inside of the sheath 1305 to release from the male threaded hub 1308. The male threaded hub 1308, and thus the clip 1301, are now free from the sheath 1305 and the rest of the delivery device. As shown in FIG. 13C, the outer sleeve 1303 remains connected to the control wire 1304 at connection point 1310, and both can be removed with the sheath 1305. The distal portion of control wire 1304 is bent towards, and connects with, outer sleeve 1303 at connection point 1310. The distal portion of control wire 1304 passes male threaded hub 1308 during deployment through slot 1309 in male threaded hub 1308.

FIGS. 14A, 14B, and 14C show an alternative embodiment of the present invention. In the embodiment of FIGS. 14A, 14B, and 14C, the relaxed state of the clip is closed, and it is forced open and allowed to close naturally. FIG. 14A shows a side view of the clip 1401 in a closed, pre-released state, and FIG. 14B shows an edge view of the clip 1401 in a closed, pre-released state. In this embodiment, because the clip 1401 is manufactured such that the clip legs 1407 are naturally closed, the primary function of the control wire 1406 is changed from having to close the clip 1401, to having to open the clip 1401. The clip 1401 is manufactured in a generally x-shaped geometry, where each tab 1403 at the proximal end of the clip 1401 controls a clip leg 1407 opposite at the distal end of the clip 1401. The action/reaction of the clip 1401 is similar to that of a common clothes pin. As the tabs 1403 are brought together, the clip legs 1407 are spread apart. As the tabs 1403 are released, the clip legs 1407 come together. A u-ring 1402 attached to the end of the control wire 1406 is used to bring the tabs 1403 together, thus opening the clip 1401. Pulling on the control wire 1406 pulls the u-ring 1402 into contact with tabs 1403 creating a compressive force to open clip legs 1407 because clip 1401 is positioned against fulcrum point 1408. Advancing control wire 1406 advances u-ring 1402, thereby removing the compressive force on tabs 1403 and allowing clip legs 1407 to close. Advancing control wire 1406 further to a deployment position pushes u-ring 1402 against clip legs 1407, causing clip 1401 to move out of outer sleeve 1404 into a deployed state.

The control wire 1406 is constructed of material having a shape memory, and the distal end of the control wire 1406, where the u-ring 1402 is attached, is pre-bent to one side. While a minimum tension exists in control wire 1406, the u-ring remains around the constriction. However, when the desired location for the clip 1401 has been achieved, and the clip tabs 1403 have been advanced beyond outer sleeve 1404, the control wire 1406 can be advanced to its most distal position. Because the control wire 1406 is pre-bent, as it is advanced the u-ring 1402 becomes disengaged from the clip 1401 when the tension in control wire 1406 falls below a pre-determined amount, as shown in FIG. 14C. This allows the clip 1401 to be released.

Figure 15A:
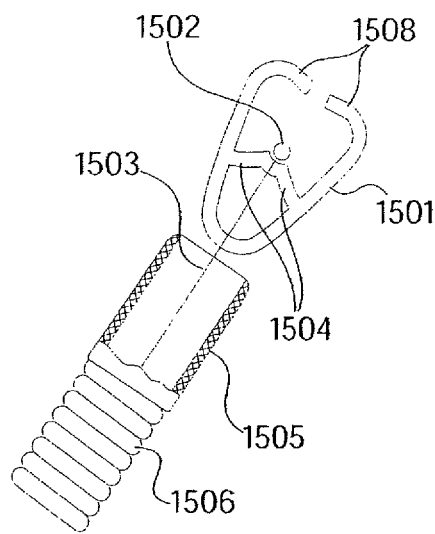
FIG. 15A is an enlarged partial view of another embodiment of the medical device of the present invention.
Figure 15B:
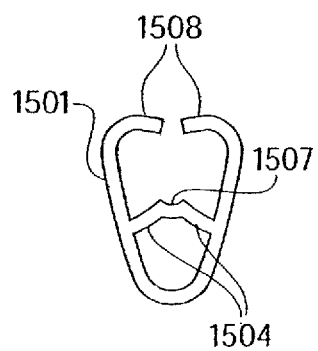
FIG. 15B is an enlarged partial view of the clip of the embodiment of FIG. 15A in a closed position.
Figure 15C:
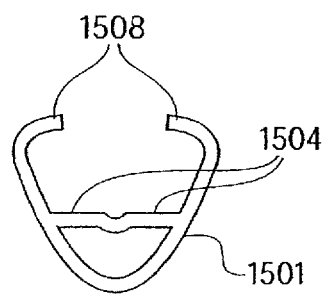
FIG. 15C is an enlarged partial view of the clip of the embodiment of FIG. 15A in an open position.
Figure 15D:
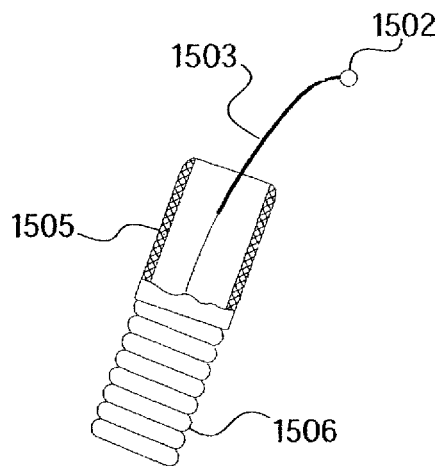
FIG. 15D is an enlarged partial view of the distal end of the medical device of the embodiment of FIG. 15A after the clip has been released.

FIGS. 15A, 15B, 15C, and 15D show another embodiment in which the clip is manufactured in a naturally closed position. FIG. 15A shows the distal end of medical device 1509 with the clip 1501 in a closed position before deployment. FIG. 15B shows only the clip 1501 in a closed position. FIG. 15C shows the clip 1501 in an open position. FIG. 15D shows the device after the clip is released. The clip 1501 is shaped such that, as the control wire 1503 is pulled in a proximal direction, the clip legs 1508 are forced apart from one another. This is accomplished using a pill 1502 attached to the end of the control wire 1503 as explained in previous embodiments. Two rigid arms 1504, located, between the clip legs 1508, translate the tensile force on the control wire 1503 to an outward radial force on the clip legs 1508. When the desired location for the clip 1501 has been achieved, the control wire 1503 can be advanced to its most distal position. Because the control wire 1503 is constructed of material that has a shape memory, and because the control wire 1503 is pre-bent close to the pill 1502, as the control wire 1503 is advanced, the pill 1502 becomes disengaged from the pill well 1507. When the pill 1502 moves out and away from the pill well 1507, the clip 1501 is released and disengages from the control wire 1502, the sheath 1506, and the outer sleeve 1505.

Figure 16A:
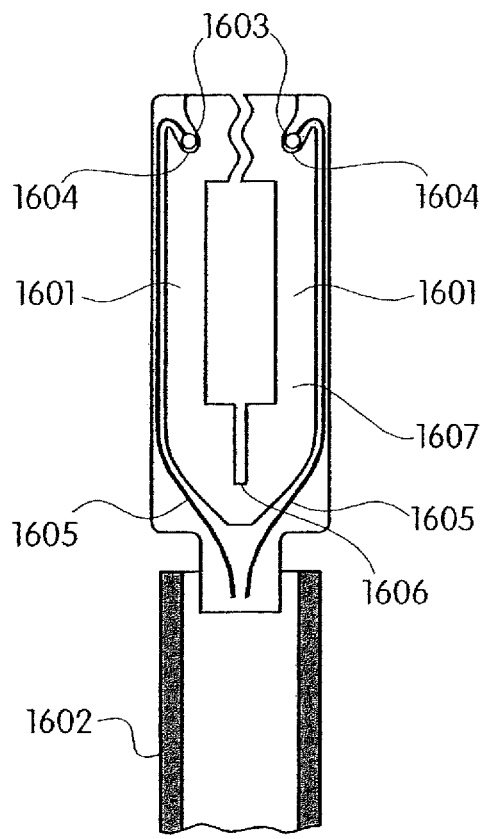
FIG. 16A is an enlarged partial view of another embodiment of the medical device of the present invention.
Figure 16B:
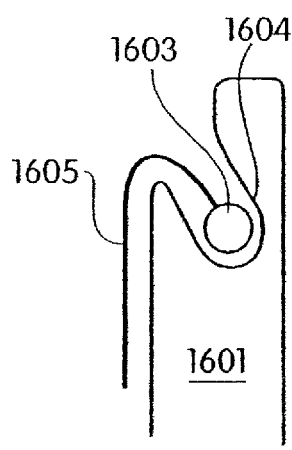
FIG. 16B is an enlarged partial close-up side view of the end of a clip leg of the embodiment of FIG. 16A.
Figure 16C:
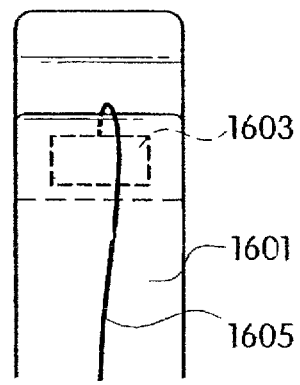
FIG. 16C is an enlarged partial close-up edge view of the end of a clip leg of the embodiment of FIG. 16A.
Figure 16D:
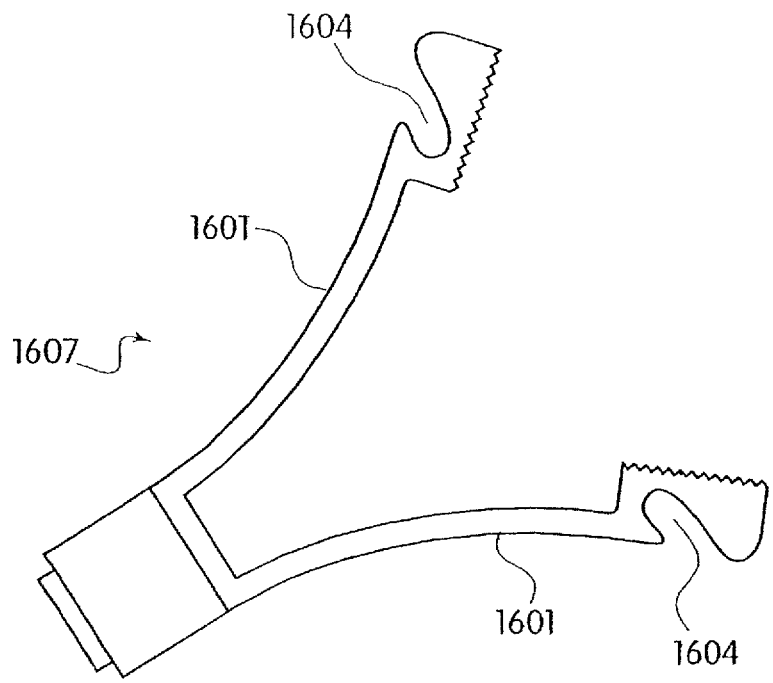
FIG. 16D is an enlarged partial view of the embodiment of FIG. 16A with the clip in an open position.
Figure 16E:
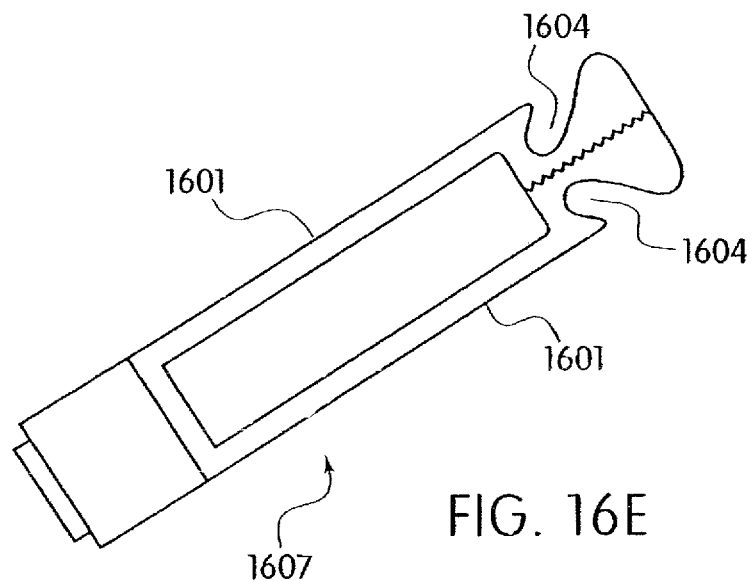
FIG. 16E is an enlarged partial view of the embodiment of FIG. 16A with the clip in a closed position.

FIGS. 16A, 16B, 16C, 16D, and 16E show another embodiment in which the clip is manufactured in a naturally closed position. FIG. 16A shows the clip 1607 in a closed, predeployed, state. FIG. 16B shows a side view of one clip leg 1601 with the pill 1603 still resting in pill well 1604. FIG. 16C shows an edge view of one clip leg 1601 with the pill 1603 still resting in pill well 1604. FIG. 16D shows a clip 1607 in an open position. FIG. 16E shows a clip 1607 in a closed position. This embodiment uses two control wires 1605. Alternatively, a branched control wire may be used. By using a branched control wire or two control wires 1605, the force can be transmitted to a point further away from the fulcrum (bending point) 1606 of the clip 1607. The greater this distance, the lesser the force required to open the clip legs 1601. As in the previous embodiments, the control wires 1605 are disengaged from the clip 1607 by pushing them forward. This action disengages the pills 1603 from the clip 1607 by moving the pills 1603 out of pill wells 1604. The control wires 1605 are made from a material with a shape memory, so that when freed from pill wells 1604, the pills 1603 move away from the pill wells 1604, and the clip 1607 is deployed.

Figure 17A:
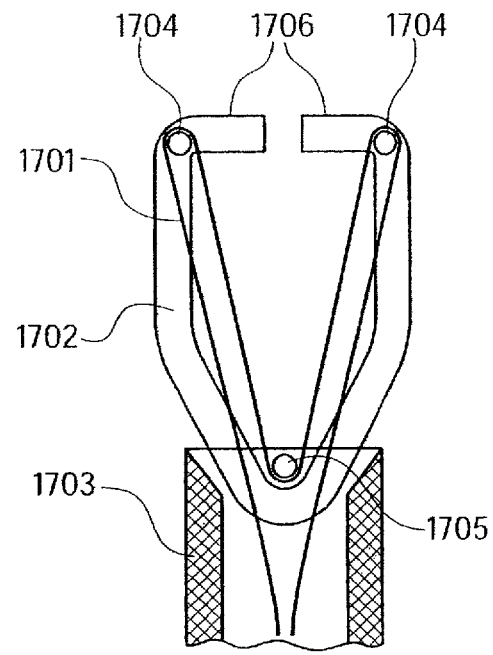
FIG. 17A is an enlarged partial view of another embodiment of the medical device of the present invention.
Figure 17B:
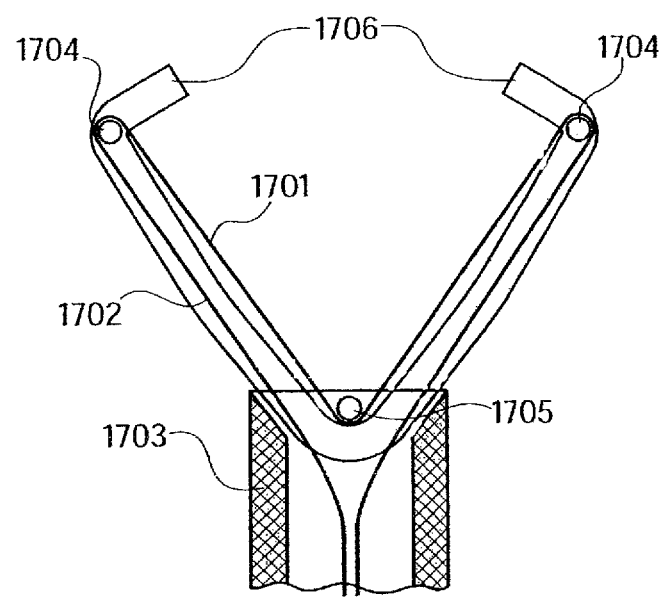
FIG. 17B is an enlarged partial view of the embodiment of FIG. 17A, showing the clip in an open position.

Another embodiment is shown in FIGS. 17A and 17B. In this embodiment, the control wire or wires 1701 are routed to gain mechanical advantage. In this embodiment, the clip 1702 is naturally closed, with the control wire(s) 1701 routed to leverage points 1704 further away from the fulcrum (bending point) 1705 of the clip 1702. In this embodiment, the control wire(s) 1701 are looped around pins positioned at leverage points 1704 at the ends of the clip legs 1706. The control wire(s) 1701 are then routed to a point at the proximal end of the clip. The control wire(s) 1701 are then terminated at this point. For ease of manufacture, the control wire(s) 1701 could essentially be one, continuous wire, with both ends terminated in the handle (not shown). To release the clip 1702, one end of control wire 1701 could be detached from the handle and pulled free from the clip 1702. Because the control wire 1701 is only wrapped around pins positioned at leverage points 1704 on the clip 1702, by pulling on one end of control wire 1701, control wire, 1701 could be easily detached when the desired location for clip 1702 has been achieved by continuing to pull on one end of control wire 1701 until all of control wire 1701 has been detached from the clip 1702.

FIGS. 18A, 18B, 18C, 18D, 18E, and 18F show an embodiment of a clip which incorporates the natural compressive forces present in a simple elastic band (or o-ring) 1802 to hold the clip legs 1801 in the closed position. FIG. 18A shows two clip legs 1801 in a disassembled state. FIG. 18B shows a clip with the control wire 1803 engaging a second elastic band 1804 to open clip legs 1801. In this embodiment, the control wire 1803 is attached to the proximal end of the clip legs 1801 via a frangible link. In this embodiment, the frangible link is a second elastic band (or o-ring) 1804 that will deform as the control wire 1803 is pulled back. In this embodiment, the clip is housed in the end of a sheath 1806 such that, as the control wire 1803 is pulled back, the second elastic band 1804 delivers an increasing compressive force to the clip legs 1801 proximal to a pin joint 1805, thereby causing the clip legs 1801 distal from the pin joint to open against the compressive force of elastic band 1802. In this manner, the clip legs 1801 move to an open position, as shown in FIG. 18B. FIG. 18C shows the clip in a closed, predeployed state. FIG. 18D shows a profile view of clip legs 1801, and FIG. 18E shows an end-on view of clip legs 1801 within sheath 1806. FIG. 18F shows a close-up view of clip legs 1801 without first elastic band 1802 but showing band slots 1809. FIG. 18F shows second elastic band 1804 resting over nubs 1807 and coupled to control wire 1803. When the desired clip location has been achieved, the second elastic band 1804, which makes up the frangible link, is overcome by pulling the control wire 1803 to its most proximal position. This has the effect of breaking second elastic band 1804. Alternatively, second elastic band 1804 could be designed to release over nubs 1807. In a third alternative, after placing clip legs 1801 in the desired location, control wire 1803 can be released so that elastic band 1802 again closes clip legs 1801. In this third embodiment, control wire 1803 is made of a suitable material, such as a shape memory material, and has a bend in the distal region such that moving control wire 1803 to a maximum distal position acts to unhook hook 1808 from second elastic band 1804.

Figure 19C:
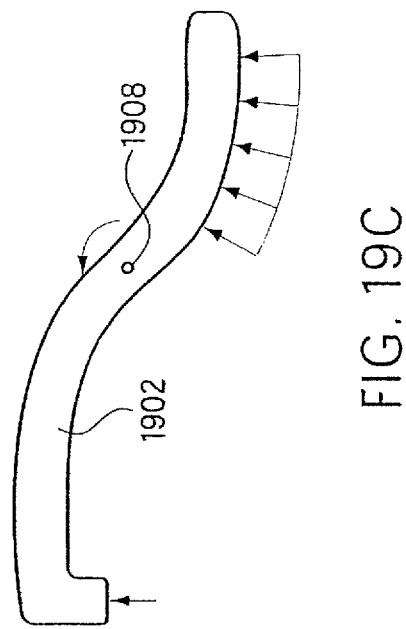
FIG. 19C is an enlarged partial view of a clip leg of the embodiment of FIG. 19A.
Figure 19A:
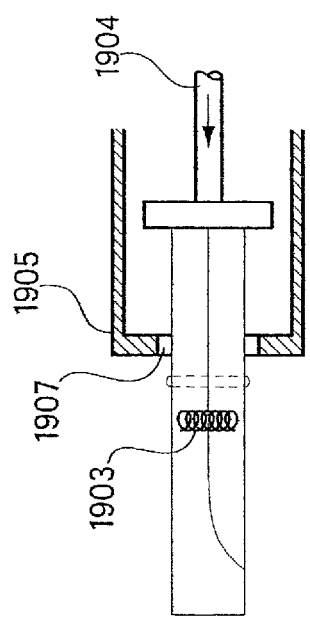
FIG. 19A is an enlarged partial edge view of another embodiment of the medical device of the present invention.
Figure 19B:
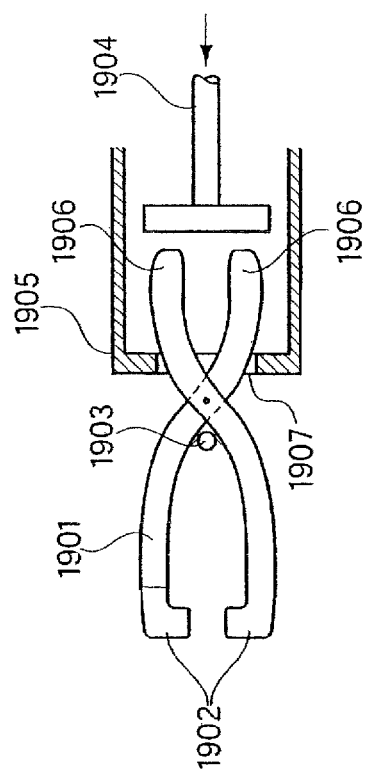
FIG. 19B is an enlarged partial side view of the embodiment of FIG. 19A.

FIGS. 19A, 19B, and 19C show another embodiment of the invention utilizing a naturally closed clip. Clip 1901 is held in the naturally closed position by a torsion spring 1903. The clip 1901 is actuated from the closed to the opened position in a different way than prior embodiments. A plunger 1904, located within the outer sleeve 1905 at the end of the sheath (not shown), is used to push on the tabs 1906 on the proximal end of the clip 1901. The tabs 1906 are pushed through an opening 1907 in the end of the outer sleeve 1905. This moves tabs 1906 close together, in turn moving the clip legs 1902 to the open position. When the desired clip location has been achieved, the clip 1901 can be released by advancing the plunger 1904 to its most distal position. FIG. 19B shows the clip 1901 from a profile view. FIG. 19C shows a single clip leg 1902 and connection point 1908 for pivotally connecting clip legs 1902 to each other.

FIGS. 20A, 20B, and 20C describe the embodiment of a three-legged clip and delivery device. The clip 2001 is manufactured to be in the naturally open position. The clip 2001 is characterized by male threads 2002 on its outer surface. The delivery device consists of a sheath 2003 similar to those described in previous embodiments. An inner sleeve 2004 located within the distal end of the sheath 2003 is used to actuate the clip 2001 from its naturally open position to the closed position. The inner sleeve 2004 has female threads (not shown) on its inside diameter. A control wire (not shown) is used in this device to transmit rotational force rather than tensile/compressive force. Rotating the sheath 2003 with respect to the control wire, with the handle (not shown) actuates the clip 2001. This rotation force is translated to the female threads, causing them to be threaded onto the clip 2001. As the naturally open clip legs 2005 move toward the inner sleeve 2004, the clip legs 2005 are closed. The clip 2001 and inner sleeve 2004 are released from the sheath 2003 via some form of frangible link (not shown) as described in the previous embodiments. FIG. 20A shows the clip legs 2005 and inner sleeve 2004 from the perspective of the target area. FIG. 20C shows the size relationship between the female threads on the inner sleeve 2004 and the male threads 2002 on the clip 2001.

Figure 21:
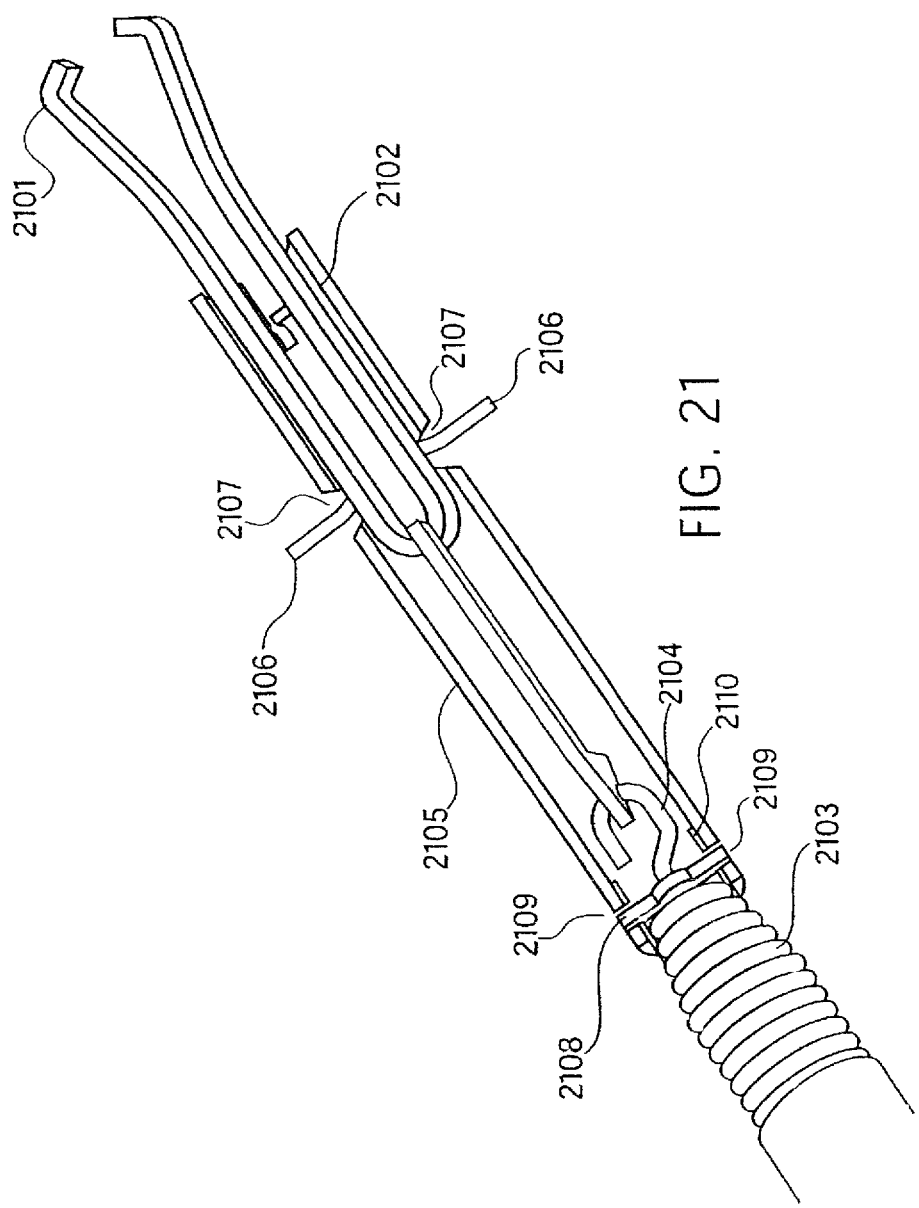
FIG. 21 is an enlarged partial view of the distal end of another embodiment of the medical device of the present invention.

FIG. 21 shows another embodiment of a naturally open clip and delivery device. FIG. 21 shows the distal portion of the medical device with a portion of the outer sleeve 2102 cut away to show the inner mechanics of the clipping device. The delivery device consists of a sheath 2103 similar to those described in previous embodiments. The clip 2101 is actuated from the open to the closed position via a control wire 2104, as described in the primary embodiment. A frangible link is implemented in this embodiment by a breakable link 2105. In this embodiment the lock sleeve is eliminated. Eliminating the lock sleeve reduces the number of components and the overall size of the device. In this embodiment the outer sleeve 2102 is used to hold the clip 2101 in the closed position. Therefore, the outer sleeve 2102 must be deployed from the sheath 2103 when the clip 2101 is released. To create a positive mechanical lock between the clip 2101 and outer sleeve 2102, the clip 2101 has two deformable tabs 2106 formed in its proximal end. When the desired tissue purchase has been accomplished, the control wire 2104 is further actuated by the handle (not shown) so that the tabs 2106 reach a position where they are in the same plane as the cut-outs 2107 in the outer sleeve 2102. Once the tabs 2106 have reached this point, further actuation of the control wire 2104 forces the tabs 2106 to deform through the cut-outs 2107 in the outer sleeve 2102.

As in the first embodiment, a retainer 2108 is used to create a mechanical lock between the sheath 2103 and outer sleeve 2102. In this embodiment the retainer 2108 passes through slots 2109 in the outer sleeve 2102 and a sheath connector 2110. The sheath connector 2110 is simply a rigid connector, applied to the end of the sheath 2103 by some means known in the art (e.g. welding, adhesive, swaging, etc.). As the tabs 2106 become engaged, a tensile load in the control wire 2104 is translated to the breakable link 2105. At a predetermined tensile load, the breakable link 2105 breaks. As the control wire 2104 is further actuated, a distal portion of control wire 2104, which is preformed into a shape that will function as a retainer release, engages the retainer 2108. The retainer 2108 is pulled from the outer sleeve 2102 by the control wire 2104, in a similar manner to that described in the primary embodiment. Once this is done, the sheath connector 2110 (and therefore the sheath 2103) is released from the outer sleeve 2102.

The materials utilized in construction of the clip of the present invention include many bio-compatible materials (metals, polymers, composites, etc.). A stainless steel grade material, which offers good spring properties, may be used. The clip can also be coated, or plated, with a material like gold to improve. radiopacity.

The lock sleeve, lock pawls, retainer and outer sleeve may be comprised of any of the same materials as the clip component. For example, stainless steel may be used.

The control wire in the first embodiment may be a stainless steel wire. Because the wire must offer sufficient strength in both tension and compression, the material properties of the wire are important to the functionality of the device. Also, the end of the wire, where the j-hook is formed, must deform when a predetermined tensile load is applied. The device's ability to release the clip is dependent on this property. Other embodiments of the device may incorporate a two (or more) piece wire so that certain sections of the wire have different material properties or geometries. Different material properties or geometries could allow for more control over how and when the wire detaches from the distal tip of the device. This could also be accomplished by several other methods, as well. For example, localized heat treating and/or coatings could be used along portions of the wire to alter the material characteristics. Additionally, some embodiments of the present invention require a control wire constructed of a material with a shape memory.

The sheath, in the first embodiment, is made up of several round, stainless steel wires, wound in a helical pattern to create a hollow, semi-rigid shaft. Sheaths made in this fashion are well known in the prior art. In other embodiments, the sheath could be made up of non-round wires. Other embodiments may be made up of one or more wires formed in a pattern other than a single helix, as in the first embodiment. A multiple helix or braided pattern may be used. The sheath may also be coated with a protective coating of Polytetrafluoroethylene (PTFE), or similar materials. The use of such coatings could be used to alter the flexibility of the shaft. Such coatings could also be used to increase the lubricity (decrease the coefficient of friction) between the endoscope working channel and the device. Similar materials could also be used to encapsulate the sheath's base material. This would create a matrix material, providing a combination of material properties not feasible with one single material. Other embodiments may use materials other than stainless steel as the base material. Materials such as titanium, nitinol, and/or nylon fibers may be incorporated.

A method of using the endoscopic hemostatic clipping device is provided. The method involves placing an endoscope in a body cavity as is known in the art. The device provided herein is then inserted through the endoscope. At the distal end, the endoscope is positioned near the target area. As noted above, the target area may be a lesion, a bleeding ulcer, a tumor, other abnormality, or any number of other tissues to be pinched, marked, tagged, or to which the operator wishes to apply a pinching pressure for whatever reason. The device provided is then positioned so that the clip legs embrace the target area, then the actuator is activated to close the clip legs. The success or failure of the application of pressure can be reviewed through the optical components provided separately in the endoscope. If the pinching is unsuccessful or only marginally successful, the clip legs of the device may be opened by reversing the actuation of the activator. Alternatively, if the pinching is successful, and the operator wishes to deploy the device, the actuator is fully activated, or the alternative deployment activator is activated. Finally, the remaining portion of the medical device and the endoscope are removed from the body.

It will be obvious to those skilled in the art, having regard to this disclosure, that other variations on this invention beyond those specifically exemplified here may be made. These variations include, but are not limited to, different combinations of clips, closing mechanisms, locking mechanisms, frangible links, and clip leg formations. Such variations are, however, to be considered as coming within the scope of this invention as limited solely by the following claims.

What is claimed is:

1. An endoscopic clipping device, comprising:
   a clip having first and second clip legs, the legs having first and second cutouts extending through respective proximal portions thereof;
   a control wire coupled to the clip and reversibly operable to move the first and second clip legs between an open configuration in which distal ends of the first and second legs are separated from one another and a closed configuration in which the distal ends of the first and second legs are drawn together to grip tissue located therebetween, the control wire including a hook at a distal end thereof, the hook being configured to be releasably received within the first and second cutouts of the clip;
   an axially rigid sheath enclosing the control wire, the sheath configured to communicate a first force opposing a second force of the control wire;
   a handle coupled to the axially rigid sheath; and
   an actuator coupled to the control wire and configured to move the first and second clip legs between the open and closed configurations, application of a predetermined force to the actuator applying a force to the control wire sufficient to disengage the hook from the first and second cutouts and separate the control wire from the clip.

2. The clip of claim 1, wherein the control wire and the clip are non-rotatably coupled to the sheath.

3. The clip of claim 2, further comprising a lock sleeve slidably received around the clip and an outer sleeve slidably mounted over the lock sleeve, movement of the outer sleeve distally over the lock sleeve moving the lock sleeve distally over the first and second legs to maintain the first and second legs in the closed configuration.

4. The clip of claim 3, wherein the lock sleeve comprises a lock pawl configured to lockingly engage first and second lock holes extending through the first and second legs to lock the clip in the closed configuration.

5. The clip of claim 4, further comprising a retainer configured to releasably engage the control wire with the lock sleeve, the retainer having an opening extending longitudinally therethrough to receive the control wire and first and second retainer tabs extending radially thereoutof to releasably engage first and second retainer holes in the outer sleeve.

6. The clip of claim 5, wherein the hook is positioned distally of the retainer opening.

7. The clip of claim 6, wherein the application of a proximally directed force to the control wire causes the hook to apply the proximally directed force to the retainer to disengage the retainer tabs from the lock sleeve and the hook to subsequently become straightened and disengage from the first and second cut-outs of the clip.

8. The clip of claim 7, wherein a magnitude of the proximally directed force required to cause straightening of the hook of the control wire is greater than a load required to lockingly grasp tissue between the first and second clip legs.

9. The clip of claim 3, wherein the first and second legs are biased toward the open configuration so that, movement of the outer sleeve proximally relative to the clip pulls the lock sleeve away from the clip permitting the clip to move to the open configuration.

10. The clip of claim 3, wherein the lock sleeve comprises a lock sleeve cut-out on a distal end thereof to permit withdrawal of a proximal portion of the clip thereinto.

11. The clip of claim 1, wherein the first and second clip legs have a rectangular cross-section.

12. The clip of claim 1, wherein the actuator is configured to pivot about a pivot point to apply a mechanical movement force to the control wire.

13. A device for causing hemostasis, comprising:
   a clip having first and second clip legs, the legs having first and second cutouts extending through respective proximal portions thereof;
   a control wire coupled to the clip and reversibly operable to move the first and second clip legs between an open configuration in which distal ends of the first and second legs are separated from one another and a closed configuration in which the distal ends of the first and second legs are drawn together to grip tissue located therebetween, the control wire including a hook at a distal end thereof, the hook being configured to be releasably received within the first and second cutouts of the clip;
   an actuator coupled to the control wire and configured to move the first and second clip legs between the open and closed configurations, application of a predetermined force to the actuator applying a force to the control wire sufficient to disengage the hook from the first and second cutouts and separate the control wire from the clip; and
   an outer sleeve receiving a portion of the clip including the first and second cutouts.

14. The device of claim 13, further comprising a lock sleeve slidably received around the clip, wherein the outer sleeve is slidably mounted over the lock sleeve so that movement of the outer sleeve distally over the lock sleeve moves the lock sleeve distally over the first and second legs to maintain the first and second legs in the closed configuration.

15. The device of claim 14, wherein the lock sleeve comprises a lock pawl configured to lockingly engage first and second lock holes extending through the first and second legs to lock the clip in the closed configuration.

16. A method for causing hemostasis, comprising:
   inserting a clipping device to a target position in a body adjacent target tissue to be clipped, the clipping device comprising a clip having first and second clip legs, the legs having first and second cutouts extending through respective proximal portions thereof, a control wire coupled to the clip and reversibly operable to move the first and second clip legs between an open configuration in which distal ends of the first and second legs are separated from one another and a closed configuration in which the distal ends of the first and second legs are drawn together to grip tissue located therebetween, the control wire including a hook at a distal end thereof, the hook being configured to be releasably received within the first and second cutouts of the clip, an axially rigid sheath enclosing the control wire, the sheath configured to communicate a first force opposing a second force of the control wire, actuating an actuator coupled to the control wire to grasp the target tissue between the first and second clip legs, the actuator being configured to move the first and second clip legs between the open and closed configurations, the actuator being provided on a handle coupled to the axially rigid sheath; and actuating the actuator to apply a proximally directed force to the control wire to disengage the hook from the first and second cutouts and separate the control wire from the clip.

17. The method of claim 16, wherein the clipping device comprises a retainer configured to releasably engage the control wire with the lock sleeve, the retainer having an opening extending therethrough to receive the control wire and first and second retainer tabs extending radially thereoutof to releasably engage first and second retainer holes in the outer sleeve.

18. The method of claim 17, wherein the hook is positioned distally of the retainer opening and configured to apply the proximally directed force to the retainer to disengage the retainer tabs from the lock sleeve.

* * * * *